US006926763B2

(12) United States Patent
Wright et al.

(10) Patent No.: US 6,926,763 B2
(45) Date of Patent: Aug. 9, 2005

(54) PURINE AND ISOSTERIC ANTIBACTERIAL COMPOUNDS

(75) Inventors: George E. Wright, Worcester, MA (US); Wei-Chu Xu, Worcester, MA (US); Neal C. Brown, Greenfield, NH (US)

(73) Assignee: GLSynthesis, Inc., Worcester, MA (US)

( * ) Notice: Subject to any disclaimer, the term of this patent is extended or adjusted under 35 U.S.C. 154(b) by 89 days.

(21) Appl. No.: 10/364,024

(22) Filed: Feb. 10, 2003

(65) Prior Publication Data

US 2004/0014773 A1 Jan. 22, 2004

Related U.S. Application Data

(60) Provisional application No. 60/354,961, filed on Feb. 8, 2002, provisional application No. 60/354,989, filed on Feb. 8, 2002, and provisional application No. 60/417,717, filed on Oct. 10, 2002.

(51) Int. Cl.[7] .................... C07D 473/18; A61K 31/522; A61P 31/04; C09D 5/14

(52) U.S. Cl. .................... 106/18.32; 544/276; 544/118; 514/234.2; 514/263.2; 514/263.37

(58) Field of Search ................. 544/276, 118; 514/234.2, 263.2, 263.37; 106/18.32

(56) References Cited

U.S. PATENT DOCUMENTS

| 5,516,905 A | 5/1996 | Brown et al. |
| 6,492,384 B1 | 12/2002 | Mederski et al. |
| 2003/0181719 A1 * | 9/2003 | Zhi et al. .................... 544/276 |

FOREIGN PATENT DOCUMENTS

| WO | WO 01/28561 | 4/2001 |
| WO | WO 01/29010 | 4/2001 |
| WO | WO 01/29045 | 4/2001 |
| WO | WO 2002102792 A1 * | 12/2002 | ......... A61K/31/185 |

OTHER PUBLICATIONS

George E. Wright, J Med. Chem 30, pp 109–116 1987.*
Ali et al. Design and Synthesis of Novel Antibacterial Agents with Inhibitory Activity against DNA Polymerase III, *Bioorg. Med. Chem. Lett.*, 2001, 11:2185–2188.
Braithewaite et al. Compilation, Alignment, and Phylogenetic Relationships of DNA Polymerases, *Nucl. Acids Res.*, 1993, 21:787–802.
Brown et al. Inhibitors of *Bacillus subtilis* DNA Polymerase III. 6–(Arylalkylamino)uracils and 6–Anilinouracils, *J. Med. Chem.*, 1977, 20:1186–1189.
Butler et al. Development of Novel Inhibitor Probes of DNA Polymerase III Based on dGTP Analogs of the HPUra Type: Base, Nucleoside and Nucleotide Derivatives of $N^2$–(3, 4–Dichlorobenzyl)guanine, *Nucl. Acids Res.*, 1990, 18:7381–7387.

De Bode et al. Deazapurine Derivatives XII Investigations on the Synthesis of 3–deazaguanine, *Recl. Trav. Chim. Pays–Bas*, 1974, 93:3–6.
Earl et al. The Synthesis of 8–aza–3–deazaguanosine [6–amino–1–(β–D–ribofuranosyl)–v–triazolo[4,5–c] pyridin–4–one] via a Novel 1, 3–dipolar Cycloaddition Reaction, *Can. J. Chem.*, 1980, 58:2550–2561.
Mederski et al. Non–peptide Angiotensin II Receptor Antagonists: Synthesis and Biological Activity of a Series of Novel 4, 5–Dihydro–4–oxo–3H–imidazo[4,5–c]pyridine Derivatives, *J. Med. Chem.*, 1994, 37:1632–1645.
Medveczky et al. Haloanilino Derivatives of Pyrimidines, Purines, and Purine Nucleoside Analogs: Synthesis and Activity against Human Cytomegalovirus, *J. Med. Chem.*, 1995, 38:1811–1819.
Rousseau et al. The Synthesis of Various Chloroimidazo[4, 5–c]pyridines and Related Derivatives, *J. Heterocycl. Chem.*, 1965, 2:196–201.
Stimac et al. The Synthesis of v–Triazolo[4,5–c]pyridine Nucleosides, *Nucleosides & Nucleotides*, 1991, 10:727–728.
Tarantino et al. 6–Anilinouracil–based Inhibitors of *Bacillus subtilis* DNA Polymerase III: Antipolymerase and Antimicrobial Structure–activity Relationships Based on Substitution at Uracil N3, *J. Med. Chem.*, 1999, 42:2035–2040.

(Continued)

Primary Examiner—Mark L. Berch
(74) Attorney, Agent, or Firm—Clark & Elbing LLP; Kristina Bieker-Brady, P.C.

(57) ABSTRACT

The invention features compounds of the formula:

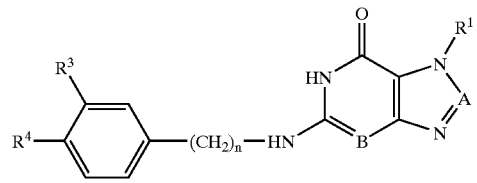

or a pharmaceutically acceptable salt thereof, wherein A is $CR^2$ and B is N; wherein n is 0–3; wherein $R^1$ is $(CH_2)_m$—$\{(G)_o$—$(CH_2)_p\}_q$—L, in which G is $CH_2$, $CH\!=\!CH$, $C\!\equiv\!C$, CO, O, S, or $NR^5$, where $R^5$ is H or $C_{1-6}$ alkyl, $CHR^6$, where $R^6$ is OH or $C_{1-6}$ alkyl, $CH(CR^7R^8)$, where each of $R^7$ and $R^8$ is, independently, H, halo, or $C_{1-6}$ alkyl, OCO, $CONR^9$, $NR^{10}CO$, where each of $R^9$ and $R^{10}$ is, independently, H or $C_{1-6}$ alkyl, $SO_2NH$, or $NHSO_2$; in which m is 1–4, o is 0–4, p is 0–4, and q is 0–4. The compounds disclosed herein have potent anti-microbial, e.g., both Gram-positive and Gram-negative anti-bacterial properties. The compounds inhibit DNA polymerase IIIC and DNA polymerase IIIE enzymes and thus act therapeutically by inhibiting the growth of a broad array of bacteria. The compounds can be administered to prevent or to treat Gram-positive or Gram-negative bacterial infections, e.g., in eukaryotic cell cultures, animals, or humans.

12 Claims, No Drawings

OTHER PUBLICATIONS

Wright et al., Inhibition of *Bacillus subtilis* DNA Polymerase III by Arylhydrazinopyrimidines, *Biochim. Biophys. Acta.,* 1976, 432:37–48.

Wright et al. DNA Polymerase III: A New Target for Antibiotic Development, *Curr. Opin. Anti–Infect. Invest. Drugs,* 1999, 1:45–48.

Xu et al. Synthesis, Properties, and Pharmacokinetic Studies of $N^2$–Phenylguanine Derivatives as Inhibitors of Herpes Simplex Virus Thymidine Kinases, *J. Med. Chem.,* 1995, 38:49–57.

* cited by examiner

PURINE AND ISOSTERIC ANTIBACTERIAL COMPOUNDS

CROSS-REFERENCE TO RELATED APPLICATIONS

This application claims benefit of U.S. Provisional Application No. 60/354,961, filed Feb. 8, 2002; U.S. Provisional Application No. 60/354,989, filed Feb. 8, 2002; and U.S. Provisional Application No. 60/417,717, filed Oct. 10, 2002, each of which is hereby incorporated by reference.

BACKGROUND OF THE INVENTION

This application relates to the field of antimicrobial compounds.

Gram-positive and Gram-negative pathogens pose a serious threat to public health. Two Gram-positive pathogens, *Staphylococcus aureus* and *Enterococcus fecalis/fecium*, are primarily nosocomial (hospital-acquired) pathogens; together, they presently account for the majority of nosocomial diseases. A third organism, *Streptococcus pneumoniae*, is generally a community-acquired pathogen. Gram-negative bacteria such as *Escherichia coli*, *Salmonella typhimurium*, and *Pseudomonas aeruginosa*, also cause significant diseases in humans.

*Staphylococcus aureus* is the most frequent cause of nosocomial bacteremia and skin/wound infection and the second most frequent cause of nosocomial lower respiratory infection. *Enterococcus fecalis/fecium* ranks third behind *Staphylococcus aureus* and *Escherichia coli* as a cause of nosocomial septicemia, endocarditis, and infections of wounds and the urinary tract. *Streptococcus pneumoniae* causes several serious and potentially life-threatening diseases. In the United States it is estimated that *Streptococcus pneumoniae* accounts annually for 6,000 cases of pneumococcal meningitis, a half million cases of pneumonia, 55,000 cases of bacteremia, and 6 million cases of otitis media. Annual mortality from *Streptococcus pneumoniae*-induced disease is estimated to be 40,000 in the United States and 3–5 million globally.

There is a rapidly growing global crisis in the clinical management of life-threatening infectious disease caused by multi-antibiotic-resistant strains of the Gram-positive pathogens *Streptococcus*, *Enterococcus*, and *Staphylococcus*, the Gram-negative pathogens *Escherichia*, *Salmonella*, and *Pseudomonas*, and certain mycoplasmata. To meet this crisis successfully, there is thus a need for new antibiotic compounds which can selectively attack novel targets in these organisms.

SUMMARY OF THE INVENTION

The invention features 2,7-disubstituted purines and their isosteres such as the corresponding 3-deazapurines and 3-deaza-8-azapurines. The compounds disclosed herein have potent anti-bacterial and anti-mycoplasmal properties. Certain of these compounds have high membrane permeability, and certain ones can form salts that are very soluble in water; thus, the compounds can therefore be administered in water or in physiological saline. The compounds described herein inhibit DNA polymerase IIIC and DNA polymerase IIIE species; the compounds thus inhibit the growth of bacteria and mycoplasmata. The compounds can be administered to prevent or to treat Gram-positive or Gram-negative bacterial or mycoplasmal infections, e.g., in eukaryotic cell cultures, animals, or humans.

In one aspect, the invention features compounds having the formula shown below:

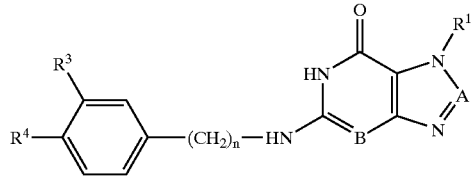

or a pharmaceutically acceptable salt thereof, wherein A and B are, independently, N or $CR^2$, in which $R^2$ is H, $C_{1-6}$ alkyl, vinyl, allyl, ethynyl, halo, $NH_2$, OH, SH, $OR^{29}$, $SR^{30}$, $NR^{31}R^{32}$, wherein $R^{29}$–$R^{32}$ are, independently, H or $C_{1-6}$ alkyl;

wherein n is 0–3;

wherein $R^3$ and $R^4$ are, independently, H, lower ($C_{1-3}$) alkyl, lower ($C_{1-3}$) polyfluoroalkyl, trifluoromethoxy or halo, or $R^3$ and $R^4$ are together —$(CH_2)_3$—;

wherein $R^1$ is $(CH_2)_m$—{$(G)_o$—$(CH_2)_p$}$_q$—L, in which G is $CH_2$, CH=CH, C≡C, CO, O, S, or $NR^5$ where $R^5$ is H or $C_{1-6}$ alkyl, $CHR^6$, where $R^6$ is OH or $C_{1-6}$ alkyl, $CH(CR^7R^8)$, where each of $R^7$ and $R^8$ is, independently, H, halo, or $C_{1-6}$ alkyl, OCO, $CONR^9$, $NR^{10}CO$, where each of $R^9$ and $R^{10}$ is, independently, H or $C_{1-6}$ alkyl, $SO_2NH$, or $NHSO_2$;

in which L is H, halo, substituted or unsubstituted $C_{1-10}$ alkyl, substituted or unsubstituted $C_{3-8}$ cycloalkyl, substituted or unsubstituted $C_6$–$C_{14}$ aryl, substituted or unsubstituted $C_{5-10}$ heteroaryl, a substituted or unsubstituted 5–8 membered non-aromatic heterocycle, $NH_2$, CN, $OR^{11}$, $SR^{12}$, $COR^{13}$, $OCOR^{14}$, $NR^{15}(CO)R^{16}$, $NR^{17}R^{18}$, $NR^{19}(CO)NHR^{20}$, $CH(CO_2R^{21})_2$, $CO_2R^{22}$, $NHSO_2R^{23}$, $CONR^{24}R^{25}$, $CH_2COR^{26}$, $S(O)R^{27}$ or $S(O_2)R^{28}$ in which each of $R^{11}$–$R^{28}$ is, independently, H, substituted or unsubstituted $C_{1-6}$ alkyl, substituted or unsubstituted $C_{3-8}$ cycloalkyl, substituted or unsubstituted $C_{6-14}$ aryl, substituted or unsubstituted $C_{7-20}$ arylalkyl, substituted or unsubstituted $C_{7-20}$ alkylaryl, or substituted or unsubstituted $C_{5-10}$ heteroaryl, in which m is 1–4, o is 0–4, p is 0–4, and q is 0–4.

In various desirable embodiments, A and B are $CR^2$ (e.g., CH); A is N and B is $CR^2$ (e.g., CH); A is $CR^2$ (e.g., CH), and B is N; or A and B are N.

In certain embodiments, n is 1, and $R^3$ and $R^4$ are, independently, fluoro, chloro, bromo, trifluoromethyl, or trifluoromethoxy. In these embodiments, $R^1$ is, for example, 4-halobutyl, 4-hydroxybutyl, 4-acetoxybutyl, 4-methoxybutyl, 4-(N-morpholinyl)butyl, 4-(N-piperidinyl)butyl, 4-(N-piperazinyl)butyl, 5-methoxypentyl, 5-ethoxypentyl, 5-propoxypentyl, 5-methylthiopentyl, 5-methylsulfoxylpentyl, or 5-methylsulfonylpentyl.

In other embodiments, n is 0, and $R^3$ and $R^4$ are, independently, H, methyl, ethyl, chloro, bromo or iodo, or $R^3$ and $R^4$ together are —$(CH_2)_3$—. In these embodiments, $R^1$ is, for example, 4-halobutyl, 4-hydroxybutyl, 4-acetoxybutyl, 4-methoxybutyl, 4-(N-morpholinyl)butyl, 4-(N-piperidinyl)butyl, 4-(N-piperazinyl)butyl, 5-methoxypentyl, 5-ethoxypentyl, 5-propoxypentyl, 5-methylthiopentyl, 5-methylsulfoxylpentyl, or 5-methylsulfonylpentyl.

In various embodiments of the above aspects, n is 1–3, and $R^3$ and $R^4$ are, independently, H, lower ($C_{1-3}$) alkyl, lower ($C_{1-3}$) polyfluoroalkyl, trifluoromethoxy, or halo.

In other desirable embodiments, n is 0; $R^3$ and $R^4$ are, independently, H, lower ($C_{1-3}$) alkyl, or halo, or $R^3$ and $R^4$ are together —$(CH_2)_3$—; or each of $R^{11}$–$R^{28}$ is, independently, H, substituted or unsubstituted $C_{1-6}$ alkyl, substituted or unsubstituted $C_{3-8}$ cycloalkyl, substituted or unsubstituted $C_{6-14}$ aryl, substituted or unsubstituted $C_{7-20}$ arylalkyl, substituted or unsubstituted $C_{7-20}$ alkylaryl, substituted or unsubstituted $C_{5-10}$ heteroaryl.

Specific compounds of the above formulae are described herein. The invention encompasses all enantiomeric and diastereomeric forms of the compounds described herein.

The invention further features pharmaceutical compositions including a compound as described above and a pharmaceutically acceptable carrier.

In another aspect, the invention features a formulation of a compound of the invention suitable for coating a surface, e.g., of a medical device as described herein. In such a formulation, the compound of the invention may be mixed with a suitable coating agent or may be covalently or other wise bound (e.g., electrostatically or as a ligand) to the coating agent.

In another aspect, the invention features a method for inhibiting bacterial growth including the step of contacting an area (e.g., media or surfaces such as those of a medical device) prone to bacterial growth with a compound of the invention. The invention also features a method for treating an animal (e.g., a mammal such as a human) for a mycoplasmal or bacterial infection (e.g., a Gram-positive or Gram-negative infection) including the step of administering to the animal a therapeutically effective amount of a compound of the invention.

In various embodiments of the invention, the compounds of the invention are useful for treating or preventing infections or inhibiting or preventing growth of *Bacillus subtilis; Staphylococcus aureus;* methicillin-resistant *Staphylococcus aureus; E. coli; Enterococcus fecalis/fecium;* vancomycin-resistant *E. fecium; Streptococcus pneumoniae, Salmonella typhimurium; Pseudomonas aeruginosa;* mycoplasmata (e.g., *Mycoplasma pneumoniae, Ureaplasma urealyticum*); others microbes in the *Bacillis, Streptococcus, Enterococcus, Staphylococcus, Escherichia, Salmonella, Pseudomonas, Mycoplasma,* and *Ureaplasma* genera; and any other microbes that produce pol IIIC or pol IIIE.

By "administration" or "administering" is meant a method of giving one or more unit doses of an antimicrobial pharmaceutical composition to an animal, e.g., a mammal (e.g., topical, oral, intravenous, intraperitoneal, or intramuscular administration). The method of administration may vary depending on various factors, e.g., the components of the pharmaceutical composition, site of the potential or actual infection, microbe involved, and severity of the actual microbial infection.

By "alkyl" is meant a branched or unbranched saturated hydrocarbon group, desirably having from 1 to 20 carbon atoms. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, aryl, and carboxyl groups.

In various embodiments of the invention the alkyl group is of 1 to 5, 1 to 10, 1 to 15, 1 to 20, 5 to 10, 5 to 15, or 10 to 15 carbon atoms. Examples include methyl; ethyl; n-propyl; isopropyl; n-butyl; iso-butyl; sec-butyl; tert-butyl; pentyl; cyclopropyl; cyclobutyl; cyclopentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; hexyl; heptyl; cyclohexyl; cycloheptyl; and cyclooctyl.

By an "animal susceptible to a microbial infection," e.g., mycoplasmal or Gram-positive or Gram-negative bacterial infection" is meant an animal that is at increased risk, relative to the general population, of contracting a microbial infection. Examples of such animals include those that have recently undergone a surgical procedure, or immunocompromised humans, e.g., those with AIDS (acquired immunodeficiency syndrome) or those having transplants for which immunosuppressive drugs are required. Such animals can be identified using methods known to one of ordinary skill in the art.

By "aryl" is meant an aromatic group having a ring system comprised of carbon atoms with conjugated π electrons (e.g., phenyl). The ring of the aryl group is desirably 6 to 18 atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "coating agent" is meant a compound or mixture of compounds suitable for coating a surface. Exemplary coating agents include polymers, e.g., poly(ethyleneglycol) or other polymers that are biocompatible. Suitable coating agents are known in the art.

By an "effective amount" of a compound is meant an amount which, when administered to a site of infection or potential infection, e.g., a medium such as a eukaryotic cell culture or a patient, will achieve a specified level of microbial inhibition or prevention of establishment of a microbial infection, respectively.

By "halo" is meant fluoro, chloro, bromo, or iodo.

By "heteroaryl" is meant an aromatic group having a ring system with conjugated π electrons (e.g., imidazole). The ring of the heteroaryl group is desirably 5 to 18 atoms selected from the group consisting of carbon, nitrogen, oxygen, sulfur, and phosphorous. Heteroaryl groups may optionally include monocyclic, bicyclic, or tricyclic rings, in which each ring desirably has five or six members. The heteroaryl group may be substituted or unsubstituted. Exemplary substituents include alkyl, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino.

By "heterocycle" is meant a cyclic group, having from 1 to 50 atoms selected from the group consisting of carbon, nitrogen, oxygen, sulfur, or phosphorous. A heterocycle may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, and carboxyl groups By "inhibiting" is meant reducing the cellular growth rate of the microbe by at least 80%. In certain embodiments, the growth can be inhibited by 90%, 95%, or even 99% or more.

The degree of inhibition can be ascertained, for example, by an in vitro growth assay, e.g., by a standard liquid culture technique. Compounds showing inhibition of colony formation at suitable MICs (minimal inhibitory concentrations), e.g., <100 µg/ml, more preferably <10 µg/ml, are useful for further examination as therapeutic agents.

By "medium" is meant any substance, e.g., a liquid or solid, on which or in which a microbe may be present or in which prevention of the presence of a microbe is desired. Exemplary media include culture media (e.g., agar or broth), food, medical supplies (e.g., sterile fluids), medical devices (e.g., catheters), countertops, and other surfaces.

By "microbial infection" is meant the invasion of a host animal, e.g., a mammal, by pathogenic microbes. For example, the infection may include the excessive growth of a microbe that is normally present in or on the body of a mammal or growth of a microbe that is not normally present in or on the mammal. More generally, a microbial infection can be any situation in which the presence of a microbial population(s) is damaging to a host animal. Thus, an animal is "suffering" from a microbial infection when an excessive amount of a microbial population is present in or on the animal's body, or when the presence of a microbial population(s) is damaging the cells or other tissue of the animal. In one embodiment, the number of a particular genus or species of microbe is at least 2, 4, 6, or 8 times the number normally found in the animal. Examples of microbes include, but are not limited to, mycoplasmata or gram positive and/or gram negative bacteria or any other class of bacteria.

By "pharmaceutically acceptable salts" are meant are meant those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal (e.g., sodium or potassium), alkaline earth metal (e.g. magnesium), ammonium and $NR_4^+$ (where R is $C_{1-4}$ alkyl) salts. Preferred salts include hydrochlorides, hydrobromides, sulfates, mesylates, maleates, tartrates, and fumarates. References hereinafter to a compound according to the invention includes compounds of the general formulae shown, as well as their pharmaceutically acceptable salts.

By "prevention" of microbial growth or infection is meant the application of a compound of the invention such that microbial growth or infection does not occur. The amount of a compound of the invention necessary for prevention of microbial growth can be ascertained, for example, by an in vitro growth assay, e.g., by a standard liquid culture technique. The amount of a compound of the invention necessary for the prevention of microbial infection may be ascertained, for example, by an in vivo assay, e.g., by determining the amount of compound that must be administered in order to prevent infection in a study animal, e.g., a guinea pig, after inoculation with a microbe. In general, compounds showing prevention at suitable concentrations, e.g., <100 µg/ml, more preferably <10 µg/ml, are useful for further examination as therapeutic agents.

By "substituted" is meant that one or more hydrogen atoms of a compound or portion of a compound are replaced by substituents, including, but not limited to, $C_{1-6}$ alkyl, $C_{3-6}$ cycloalkyl, hydroxyl, $C_{1-6}$ alkoxyl, amino, alkylamino, arylamino, heteroarylamino, carboxyl, halo, cyano, azido, $C_{6-12}$ aryl, $C_{7-20}$ arylalkyl, $C_{4-12}$ heteroaryl (e.g., $C_{4-6}$ or $C_{5-12}$ heteroaryl), C(O)—$C_{1-6}$ alkyl, C(O)—$C_{6-12}$ aryl, $(SO_2)$—$C_{1-6}$ alkyl, (SO) O—$C_{1-6}$ alkyl, $(SO_2)$—$C_{6-12}$ aryl, $(SO_2)$O—$C_{6-12}$ aryl, $(SO_2)$—$C_{5-12}$ heteroaryl, $(SO_2)$O—$C_{5-12}$ heteroaryl. The substituents can in turn be substituted with functional groups, including, but not limited to, halo, trifluoromethyl, hydroxyl, and carboxyl.

By "treating" is meant the medical management of a patient with the intent that a cure, amelioration, or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

By "therapeutically effective amount" is meant an amount which, when administered to an animal in need, will alleviate at least some of the symptoms of a bacterial infection. In the context of prophylaxis, a "therapeutically effective amount" is an amount which, when administered to an animal susceptible to bacterial infection, will help inhibit or reduce the likelihood of such an infection.

The details of one or more embodiments of the invention are set forth in the accompanying description below. Other features, objects, and advantages of the invention will be apparent from the description and from the claims.

DETAILED DESCRIPTION OF THE INVENTION

The unexpected discovery that 7-substituted 2-(arylalkylamino)purine and 7-substituted 2-phenylaminopurine compounds and, in addition, 3-deaza and 3-deaza-8-aza isosteres thereof, have potent and selective inhibitory activity against DNA polymerases IIIC or IIIE or both and the growth of Gram-positive bacteria, Gram-negative bacteria, or mycoplasmata is the basis of the present invention. Accordingly, novel compounds of these classes that possess antibacterial and anti-mycoplasmal activity as a result of inhibition of DNA polymerases IIIC and/or IIIE are disclosed. The invention further features methods of using these compounds and pharmaceutical compositions for treating Gram-positive and Gram-negative bacterial infections and mycoplasmal infections or inhibiting bacterial or mycoplasmal growth.

The general structure and numbering system employed is:

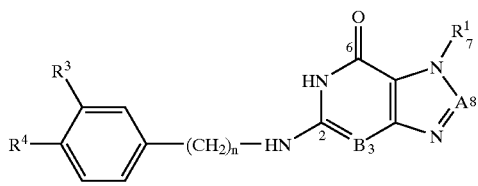

The invention features compounds having the formulae shown below:

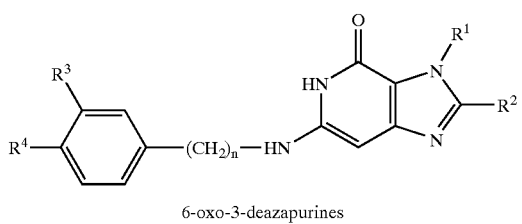

6-oxo-3-deazapurines

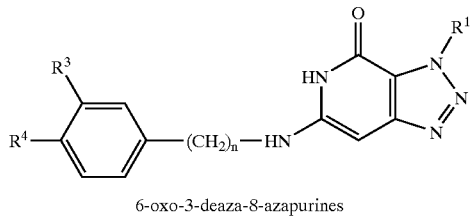

6-oxo-3-deaza-8-azapurines

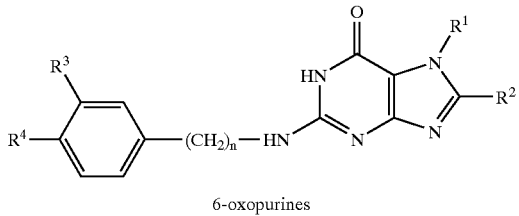

6-oxopurines

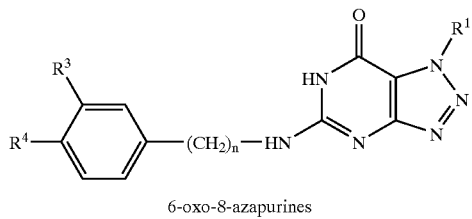

6-oxo-8-azapurines wherein n and $R^1$–$R^4$ are as defined above, and all enantiomeric and diastereomeric forms thereof, and pharmaceutically acceptable salts thereof.

In one series of embodiments of formulae I and III, n is 1, $R^3$ and $R^4$ are chloro, $R^2$ is hydrogen, $R^1$ is 4-hydroxybutyl, 4-methoxybutyl, 2-methoxyethyl, 5-methoxypentyl, 4-(N-morpholinyl)butyl, 4-(N-piperazinyl)butyl or 4-(N-piperidinyl)butyl. In another series of embodiments of formulae I and III, n is 1, $R^3$ and $R^4$ are chloro, $R^2$ is amino, methoxy or methyl, $R^1$ is 4-hydroxybutyl, 4-methoxybutyl, 2-methoxyethyl, 5-methoxypentyl, 4-(N-morpholinyl)butyl, 4-(N-piperazinyl)butyl or 4-(N-piperidinyl)butyl. In a series of embodiments of formulae II and IV, n is 1, $R^3$ and $R^4$ are chloro, $R^1$ is 4-hydroxybutyl, 4-methoxybutyl, 2-methoxyethyl, or 5-methoxypentyl.

In another series of embodiments of formulae I and III, n is 0, $R^3$ is methyl, ethyl, chloro, bromo or iodo, and $R^4$ is methyl, $R^2$ is hydrogen, $R^1$ is 4-hydroxybutyl, 2-methoxyethyl, 4-methoxybutyl, 5-methoxypentyl, 4-(N-morpholinyl)butyl, 4-(N-piperazinyl)butyl or 4-(N-piperidinyl)butyl. In another series of embodiments of formulae II and IV, n is 0, $R^3$ is methyl, ethyl, chloro, bromo or iodo, and $R^4$ is methyl, $R^1$ is 4-hydroxybutyl, 2-methoxyethyl, 4-methoxybutyl, or 5-methoxypentyl.

In some compounds of formulae I–IV, $R^3$ and $R^4$ are selected from the group consisting of methyl, ethyl, Cl, Br, I, $CF_3$, $OCF_3$, $CF_2CF_3$ and $CH_2CF_3$.

The location of $R^1$ at the 7 position affords potent inhibition of DNA polymerases IIIC, IIIE, or both and consequently, of the growth of Gram-positive bacteria, Gram-negative bacteria, mycoplasmata, or combinations thereof.

Methods of using the compounds described herein include a method of inhibiting growth of mycoplasmata or Gram-positive and Gram-negative bacteria in vitro by contacting the in vitro media with an effective amount of a compound according to this invention, and a method of treating an animal with a mycoplasmal or Gram-positive or Gram-negative bacterial infection by administering to the animal a therapeutically effective amount of a compound according to this invention. Other methods for using the compounds and compositions according to this invention will be apparent to those of ordinary skill in the art.

The compounds described herein may have special advantages in the treatment of organisms that have become resistant to currently used therapeutics. For example, these compounds can inhibit the DNA polymerase III enzymes from strains of pathogenic *Enterococci, Streptococci, Staphylococci, Escherichia, Salmonella, Pseudomonas,* and other bacteria or mycoplasmata that are resistant to currently used antibiotics. Inhibition of DNA polymerase IIIC and IIIE, the enzymes responsible for replication of the genome of the organisms, causes inhibition of growth of the organisms.

Mechanism of Action

Genome sequence analysis has indicated that organisms such as the Mycoplasmata and Gram-positive eubacteria of the so-called low G:C class, i.e., those with genomes containing a proportion of guanine+cytosine of less than 0.5, contain two types of DNA polymerase III (pol III): pol IIIC, encoded by a polC gene, and pol IIIE, encoded by one or more dnaE genes (See Braithewaite and Ito, Nucl. Acids Res. 21:787–802 (1993)). Gram-negative eubacteria, in contrast, contain only one type of DNA polymerase III, pol IIIE encoded by the dnaE gene (loc cit.). Arylalkylamino compounds of the invention inhibit both pol IIIC and pol IIIE, while phenylamino compounds of the invention inhibit pol IIIC (see Table 1).

For Gram-positive bacteria, pol IIIC and pol IIIE are both required for the replicative synthesis of DNA that accompanies the duplication of the host chromosome. For Gram-negative bacteria, pol IIIE is required for the replicative synthesis of DNA that accompanies the duplication of the host chromosome. The compounds described herein mimic purine deoxyribonucleoside-5-triphosphates and physically inhibit the DNA polymerases (see U.S. Pat. No. 5,516,905). Because certain of the compounds described herein inhibit the DNA polymerases from both mycoplasmata and Gram-positive and Gram-negative bacteria, they are useful for inhibiting the growth of these organisms, and for treating mycoplasmal and Gram-positive and Gram-negative bacterial infections.

TABLE 1

Biological activity of compounds of the invention.

| | K$_i$, µM | | | | | | MIC, µg/mL | | | |
|---|---|---|---|---|---|---|---|---|---|---|
| Cpd | B.s. pol IIIC | B.s. pol IIIE | E.c. pol IIIE | B.s. | S.a. | S.a. (Smith) | MRSA (B42876) | E. fecalis | E. fecium | VRE |
| 1 | 2.2 | 2.5 | 176 | 40 | 80 | 80 | 80 | 80 | 40 | 40 |
| 2 | 0.19 | 0.37 | 56 | 0.625 | 5 | 3.75 | 2.5 | 5 | 5 | 2.5 |
| 3 | 0.16 | 0.42 | 81 | 1.25 | 2.5 | 1.25 | 2.5 | 5 | 1.25 | 5 |
| 4 | 0.094 | 0.2 | nt | 7.5 | 20 | 10 | 20 | 20 | 15 | 10 |
| 5 | 0.1 | 0.29 | nt | 10 | 20 | 20 | 20 | 20 | 20 | 15 |
| 6 | 1.25 | 2.5 | 426 | 2.5 | 10 | 7.5 | 7.5 | 10 | 10 | 10 |
| 7 | 0.066 | 0.12 | 33 | 5 | 5 | 2.5 | 2.5 | 2.5 | 2.5 | 5 |
| 8 | 0.19 | 0.063 | 86 | 15 | 30 | 25 | 30 | 10 | 7.5 | 3.75 |
| 10 | 0.051 | 0.047 | 26 | 10 | 20 | 40 | 40 | 10 | 10 | 5 |
| 11 | 0.052 | 0.058 | 12 | 1.25 | 2.5 | 1.25 | 1.25 | 1.25 | 1.25 | 5 |
| 12 | 0.052 | 0.091 | 27 | 10 | 20 | 5 | 10 | 5 | 10 | 5 |
| 13 | 0.07 | 0.088 | 47 | 1.4 | 3.7 | 3.7 | 1.25 | 2.5 | 2.5 | 2.5 |
| 14 | 1.46 | 0.95 | 75 | 40 | 80 | 40 | 60 | 40 | 20 | 20 |
| 15 | 1.5 | inact | nt | 2.5 | 10 | 10 | 10 | 10 | 10 | 10 |
| 16 | 1.1 | inact | inact | 10 | 40 | 40 | 30 | >80 | 20 | >80 |
| 17 | 0.69 | 490 | inact | 1.25 | 2.5 | 2.5 | 2.5 | >80 | 2.5 | >80 |
| 18 | 0.47 | inact | nt | 15 | 30 | 40 | 30 | 20 | 20 | 10 |
| 20 | 0.28 | 318 | nt | 20 | 20 | 20 | 20 | 10 | 10 | 5 |
| 22 | 0.26 | 394 | nt | 1.25 | 5 | 5 | 2.5 | 5 | 10 | 5 |
| 23 | 0.13 | 38 | nt | 2.5 | 5 | 5 | 5 | 5 | 5 | 5 |

B.s., Bacillus subtilis; E.c., Escherichia coli; S.a., Staphylococcus aureus; MRSA, methicillin-resistant S.a.; E. fecalis, Enterococcus fecalis; E. fecium, Enterococcus fecium; VRE, vancomycin-resistant E. fecium.

Antibacterial Compounds

The compounds described herein are 7-substituted-2-(arylalkylamino)purines, 7-substituted-2-(phenylamino) purines, and their isosteres, for example, 7-substituted-2-benzylamino-6-oxo-3-deazapurines, 7,8-disubstituted-2-benzylamino-6-oxo-3-deazapurines, 7-substituted-2-benzylamino-6-oxo-3-deaza-8-azapurines, 7-substituted-2-phenylamino-6-oxo-3-deazapurines, 7,8-disubstituted-2-phenylamino-6-oxo-3-deazapurines, 7-substituted-2-phenylamino-6-oxo-3-deaza-8-azapurines, 7-substituted-2-benzylamino-6-oxopurines, 7,8-disubstituted-2-benzylamino-6-oxopurines, 7-substituted-2-benzylamino-6-oxo-8-azapurines, 7-substituted-2-phenylamino-6-oxopurines, 7,8-disubstituted-2-phenylamino-6-oxopurines, and 7-substituted-2-phenylamino-6-oxo-8-azapurines.

Preferred arylalkylamino compounds include:

2-(3,4-dichlorobenzylamino)-7-(4-hydroxybutyl)-6-oxo-3-deazapurine;
2-(3,4-dichlorobenzylamino)-7-(4-methoxybutyl)-6-oxo-3-deazapurine;
2-(3,4-dichlorobenzylamino)-7-[4-(N-morpholinyl)butyl]-6-oxo-3-deazapurine;
2-(3,4-dichlorobenzylamino)-7-(2-hydroxyethyl)-6-oxo-3-deazapurine;
2-(3,4-dichlorobenzylamino)-7-(2-methoxyethyl)-6-oxo-3-deazapurine;
2-(3,4-dichlorobenzylamino)-7-(5-methoxypentyl)-6-oxo-3-deazapurine;
2-(3,4-dichlorobenzylamino)-7-(5-ethoxypentyl)-6-oxo-3-deazapurine;
2-(3,4-dichlorobenzylamino)-7-(5-propoxypentyl)-6-oxo-3-deazapurine;
2-(3,4-dichlorobenzylamino)-7-(5-methylthiopentyl)-6-oxo-3-deazapurine;
2-(3,4-dichlorobenzylamino)-7-(5-methylsulfoxylpentyl)-6-oxo-3-deazapurine;
2-(3,4-dichlorobenzylamino)-7-(5-methylsulfonylpentyl)-6-oxo-3-deazapurine;
2-(3,4-dichlorobenzylamino)-7-[4-(N-piperazinyl)butyl]-6-oxo-3-deazapurine;
2-(3,4-dichlorobenzylamino)-7-(4-hydroxybutyl)-6-oxo-3-deaza-8-azapurine;
2-(3,4-dichlorobenzylamino)-7-(4-methoxybutyl)-6-oxo-3-deaza-8-azapurine;
2-(3,4-dichlorobenzylamino)-7-[4-(N-morpholinyl)butyl]-6-oxo-3-deaza-8-azapurine;
2-(3,4-dichlorobenzylamino)-7-(2-hydroxyethyl)-6-oxo-3-deaza-8-azapurine;
2-(3,4-dichlorobenzylamino)-7-(2-methoxyethyl)-6-oxo-3-deaza-8-azapurine;
2-(3,4-dichlorobenzylamino)-7-(5-methoxypentyl)-6-oxo-3-deaza-8-azapurine;
2-(3,4-dichlorobenzylamino)-7-(5-ethoxypentyl)-6-oxo-3-deaza-8-azapurine;
2-(3,4-dichlorobenzylamino)-7-(5-methylthiopentyl)-6-oxo-3-deaza-8-azapurine;
2-(3,4-dichlorobenzylamino)-7-(5-methylsulfoxylpentyl)-6-oxo-3-deaza-8-azapurine;
2-(3,4-dichlorobenzylamino)-7-(5-methylsulfonylpentyl)-6-oxo-3-deaza-8-azapurine;
2-(3,4-dichlorobenzylamino)-7-[4-(N-piperazinyl)butyl]-6-oxo-3-deaza-8-azapurine;
2-(3,4-dichlorobenzylamino)-7-(4-methoxybutyl)-6-oxopurine;
2-(3,4-dichlorobenzylamino)-7-[4-(N-morpholinyl)butyl]-6-oxopurine;
2-(3,4-dichlorobenzylamino)-7-(2-methoxyethyl)-6-oxopurine;
2-(3,4-dichlorobenzylamino)-7-(5-methoxypentyl)-6-oxopurine;
2-(3,4-dichlorobenzylamino)-7-(5-ethoxypentyl)-6-oxopurine;
2-(3,4-dichlorobenzylamino)-7-(5-propoxypentyl)-6-oxopurine;
2-(3,4-dichlorobenzylamino)-7-(5-methylthiopentyl)-6-oxopurine;
2-(3,4-dichlorobenzylamino)-7-(5-methylsulfoxylpentyl)-6-oxopurine;
2-(3,4-dichlorobenzylamino)-7-(5-methylsulfonylpentyl)-6-oxopurine;

2-(3,4-dichlorobenzylamino)-7-(4-methoxybutyl)-6-oxo-8-azapurine;
2-(3,4-dichlorobenzylamino)-7-[4-(N-morpholinyl)butyl]-6-oxo-8-azapurine;
2-(3,4-dichlorobenzylamino)-7-[4-(N-piperazinyl)butyl]-6-oxo-8-azapurine;
2-(3,4-dichlorobenzylamino)-7-(5-methoxypentyl)-6-oxo-8-azapurine;
2-(3,4-dichlorobenzylamino)-7-(5-ethoxypentyl)-6-oxo-8-azapurine;
2-(3,4-dichlorobenzylamino)-7-(5-propoxypentyl)-6-oxo-8-azapurine;
2-(3,4-dichlorobenzylamino)-7-(5-methylthiopentyl)-6-oxo-8-azapurine;
2-(3,4-dichlorobenzylamino)-7-(5-methylsulfoxylpentyl)-6-oxo-8-azapurine; and
2-(3,4-dichlorobenzylamino)-7-(5-methylsulfonylpentyl)-6-oxo-8-azapurine;

Preferred phenylamino compounds include:
2-(3-ethyl-4-methylphenylamino)-7-(4-hydroxybutyl)-6-oxo-3-deazapurine;
2-(3-ethyl-4-methylphenylamino)-7-(4-methoxybutyl)-6-oxo-3-deazapurine;
2-(3-ethyl-4-methylphenylamino)-7-[4-(N-morpholinyl)butyl]-6-oxo-3-deazapurine;
2-(3-ethyl-4-methylphenylamino)-7-(2-hydroxyethyl)-6-oxo-3-deazapurine; 2-(3-ethyl-4-methylphenylamino)-7-(2-methoxyethyl)-6-oxo-3-deazapurine;
2-(3-ethyl-4-methylphenylamino)-7-(5-methoxypentyl)-6-oxo-3-deazapurine;
2-(3-ethyl-4-methylphenylamino)-7-(5-ethoxypentyl)-6-oxo-3-deazapurine;
2-(3-ethyl-4-methylphenylamino)-7-(5-propoxypentyl)-6-oxo-3-deazapurine;
2-(3-ethyl-4-methylphenylamino)-7-(5-methylthiopentyl)-6-oxo-3-deazapurine;
2-(3-ethyl-4-methylphenylamino)-7-(5-methylsulfoxylpentyl)-6-oxo-3-deazapurine;
2-(3-ethyl-4-methylphenylamino)-7-(5-methylsulfonylpentyl)-6-oxo-3-deazapurine;
2-(3-ethyl-4-methylphenylamino)-7-[4-(N-piperazinyl)butyl]-6-oxo-3-deazapurine;
2-(3,4-dimethylphenylamino)-7-(4-methoxybutyl)-6-oxo-3-deazapurine;
2-(3,4-dimethylphenylamino)-7-[4-(N-morpholinyl)butyl]-6-oxo-3-deazapurine;
2-(3,4-dimethylphenylamino)-7-(2-methoxyethyl)-6-oxo-3-deazapurine;
2-(3-chloro-4-methylphenylamino)-7-(4-hydroxybutyl)-6-oxo-3-deazapurine;
2-(3-chloro-4-methylphenylamino)-7-(4-methoxybutyl)-6-oxo-3-deazapurine;
2-(3-chloro-4-methylphenylamino)-7-[4-(N-morpholinyl)butyl]-6-oxo-3-deazapurine;
2-(3-chloro-4-methylphenylamino)-7-(2-hydroxyethyl)-6-oxo-3-deazapurine;
2-(5-indanylamino)-7-(4-hydroxybutyl)-6-oxo-3-deazapurine;
2-(5-indanylamino)-7-(4-methoxybutyl)-6-oxo-3-deazapurine;
2-(5-indanylamino)-7-[4-(N-morpholinyl)butyl]-6-oxo-3-deazapurine;
2-(3-ethyl-4-methyphenylamino)-7-(-5-methoxypentyl)-8-methyl-6-oxo-3-deazapurine;
2-(3-ethyl-4-methylphenylamino)-7-(4-methoxybutyl)-8-amino-6-oxo-3-deazapurine;
2-(3-ethyl-4-methylphenylamino)-7-[5-methoxypentyl]-8-chloro-6-oxo-3-deazapurine;
2-(3-ethyl-4-methylphenylamino)-7-[4-methoxybutyl]-8-methoxy-6-oxo-3-deazapurine;
2-(3-ethyl-4-methylphenylamino)-7-(4-hydroxybutyl)-6-oxo-3-deaza-8-azapurine;
2-(3-ethyl-4-methylphenylamino)-7-(4-methoxybutyl)-6-oxo-3-deaza-8-azapurine;
2-(3-ethyl-4-methylphenylamino)-7-[4-(N-morpholinyl)butyl]-6-oxo-3-deaza-8-azapurine;
2-(3-ethyl-4-methylphenylamino)-7-(2-methoxyethyl)-6-oxo-3-deaza-8-azapurine;
2-(3-ethyl-4-methylphenylamino)-7-(5-methoxypentyl)-6-oxo-3-deaza-8-azapurine;
2-(3-ethyl-4-methylphenylamino)-7-(5-ethoxypentyl)-6-oxo-3-deaza-8-azapurine;
2-(3-ethyl-4-methylphenylamino)-7-(5-propoxypentyl)-6-oxo-3-deaza-8-azapurine;
2-(3-ethyl-4-methylphenylamino)-7-(5-methylthiopentyl)-6-oxo-3-deaza-8-azapurine;
2-(3-ethyl-4-methylphenylamino)-7-(5-methylsulfoxylpentyl)-6-oxo-3-deaza-8-azapurine;
2-(3-ethyl-4-methylphenylamino)-7-(5-methylsulfonylpentyl)-6-oxo-3-deaza-8-azapurine;
2-(3-ethyl-4-methylphenylamino)-7-[4-(N-piperazinyl)butyl]-6-oxo-3-deaza-8-azapurine;
2-(3,4-dimethylphenylamino)-7-(4-hydroxybutyl)-6-oxo-3-deaza-8-azapurine;
2-(3,4-dimethylphenylamino)-7-(4-methoxybutyl)-6-oxo-3-deaza-8-azapurine;
2-(3,4-dimethylphenylamino)-7-[4-(N-piperazinyl)butyl]-6-oxo-3-deaza-8-azapurine;
2-(3-chloro-4-methylphenylamino)-7-(4-methoxybutyl)-6-oxo-3-deazapurine;
2-(5-indanylamino)-7-(4-hydroxybutyl)-6-oxo-3-deaza-8-azapurine;
2-(5-indanylamino)-7-(4-methoxybutyl)-6-oxo-3-deaza-8-azapurine;
2-(3-ethyl-4-methylphenylamino)-7-(4-methoxybutyl)-6-oxopurine;
2-(3-ethyl-4-methylphenylamino)-7-[4-(N-morpholinyl)butyl]-6-oxopurine;
2-(3-ethyl-4-methylphenylamino)-7-[4-(N-piperidinyl)butyl]-6-oxopurine;
2-(3-ethyl-4-methylphenylamino)-7-[4-(N-piperazinyl)butyl]-6-oxopurine;
2-(3-ethyl-4-methylphenylamino)-7-(2-methoxyethyl)-6-oxopurine;
2-(3-ethyl-4-methylphenylamino)-7-(5-methoxypentyl)-6-oxopurine;
2-(3-ethyl-4-methylphenylamino)-7-(5-ethoxypentyl)-6-oxopurine;
2-(3-ethyl-4-methylphenylamino)-7-(5-propoxypentyl)-6-oxopurine;
2-(3-ethyl-4-methylphenylamino)-7-(5-methylsulfoxylpentyl)-6-oxopurine;
2-(3-ethyl-4-methylphenylamino)-7-(5-methylsulfonylpentyl)-6-oxopurine;
2-(3-ethyl-4-methylphenylamino)-7-(4-methoxybutyl)-6-oxo-8-azapurine;
2-(3-ethyl-4-methylphenylamino)-7-[4-(N-morpholinyl)butyl]-6-oxo-8-azapurine;
2-(3,4-dimethylphenylamino)-7-[4-(N-morpholinyl)butyl]-6-oxo-8-azapurine;
2-(3-ethyl-4-methylphenylamino)-7-[4-(N-piperazinyl)butyl]-6-oxo-8-azapurine;
2-(3-ethyl-4-methylphenylamino)-7-(5-methoxypentyl)-6-oxo-8-azapurine;
2-(3-ethyl-4-methylphenylamino)-7-(5-ethoxypentyl)-6-oxo-8-azapurine;

2-(3-ethyl-4-methylphenylamino)-7-(5-propoxypentyl)-6-oxo-8-azapurine;

2-(3-ethyl-4-methylphenylamino)-7-(5-methylthiopentyl)-6-oxo-8-azapurine;

2-(3-ethyl-4-methylphenylamino)-7-(5-methylsulfoxylpentyl)-6-oxo-8-azapurine;

2-(3-ethyl-4-methylphenylamino)-7-(5-methylsulfonylpentyl)-6-oxo-8-azapurine;

2-(3,4-dimethylphenylamino)-7-(4-methoxybutyl)-6-oxo-8-azapurine;

2-(3-chloro-4-methylphenylamino)-7-(4-methoxybutyl)-6-oxo-8-azapurine; and 2-(5-indanylamino)-7-(4-methoxybutyl)-6-oxo-8-azapurine;

Methods of Synthesis

The compounds of the invention may be synthesized by methods described herein. Intermediates may be synthesized by methods that are generally available in the literature.

4,6-Dichloroimidazo[4,5-c]pyridine (A) was prepared by the method of Rousseau and Robins Heterocycl. Chem. 1965, 2, 196–201. This compound was converted to 4-benzyloxy-6-chloroimidazo[4,5-c]pyridine (B) by treatment with sodium hydroxide in refluxing benzyl alcohol.

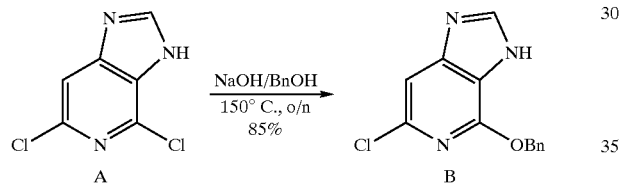

Scheme 1 illustrates the strategy for synthesis of 6-oxo-3-deazapurines of the invention. Alkylation of compound B produces two isomeric bromoalkyl intermediates B1 and B2, which are converted to the methoxyalkyl intermediates B3 and B4. The separated isomers were identified by use of two dimensional NOESY NMR spectroscopy (see below). Heating of the 7 isomer B3 with benzylamines or anilines causes amination in the 2 position and O-debenzylation to give desired compounds of the invention.

Scheme 1.
Synthesis of 7-alkoxyalkyl-2-amino-6-oxo-3-deazapurines.

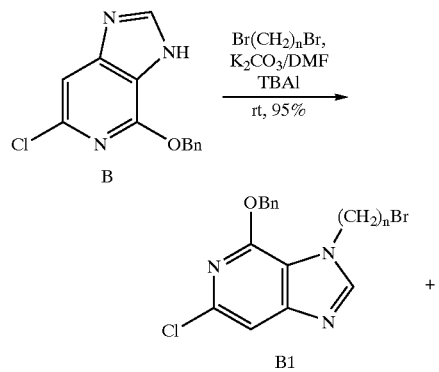

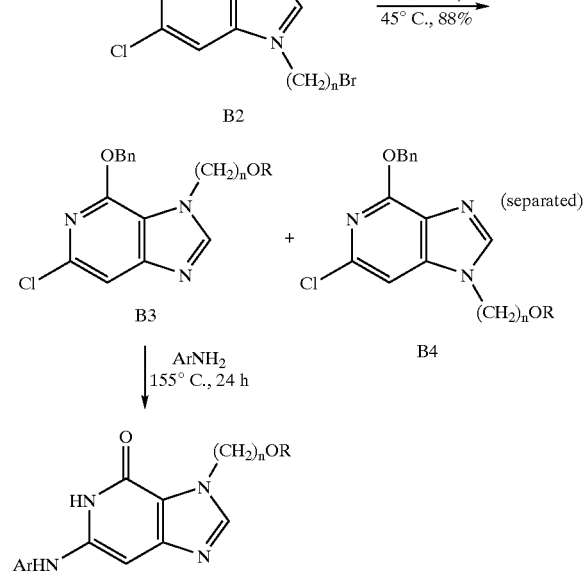

Scheme 2 illustrates the use of bromoalkyl intermediates B1 and B2 in preparation of 7-(substituted-alkyl) compounds, specifically 7-(aminoalkyl) compounds of the invention.

Scheme 2.
Synthesis of 7-aminoalkyl-2-amino-6-oxo-3-deazapurines.

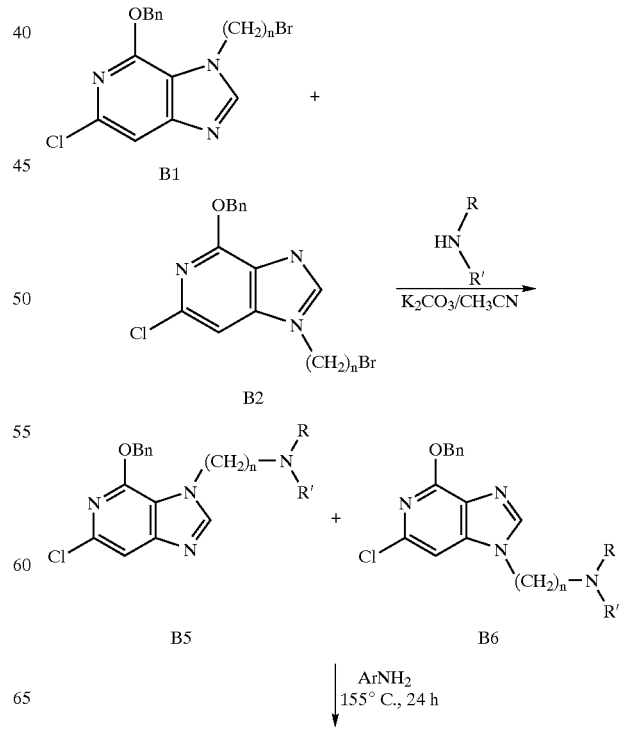

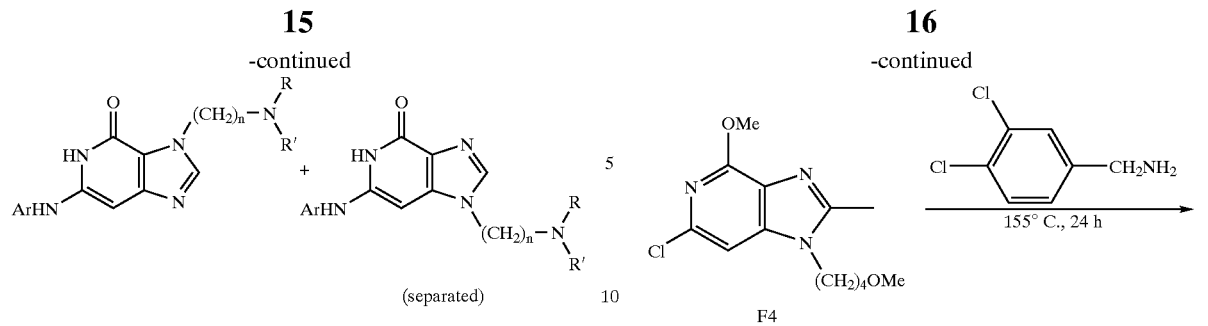

Two methods have been developed to prepare 8-alkyl-3-deazapurines of the invention. Scheme 3 summarizes the traditional alkylation method, resulting in both 7 and 9 substituted isomers, e.g. the 8-methyl compounds F1 and F2. Their conversion to the 6-methoxy intermediates F3 and F4, and fusion of the latter mixture with amines results in separable 7-alkyl-8-methyl and 9-alkyl-8-methyl products. Scheme 4 illustrates a selective ring cyclization method for 7-alkyl compounds, resulting in exclusive preparation of intermediate F3. Distinction between the 7 and 9 isomers of the 8-methyl compounds was achieved by NOESY NMR (see below), and is consistent with the structure of the isomer obtained selectively by the method of Scheme 4.

Scheme 3.
Synthesis of 8-alkyl-3-deazapurines

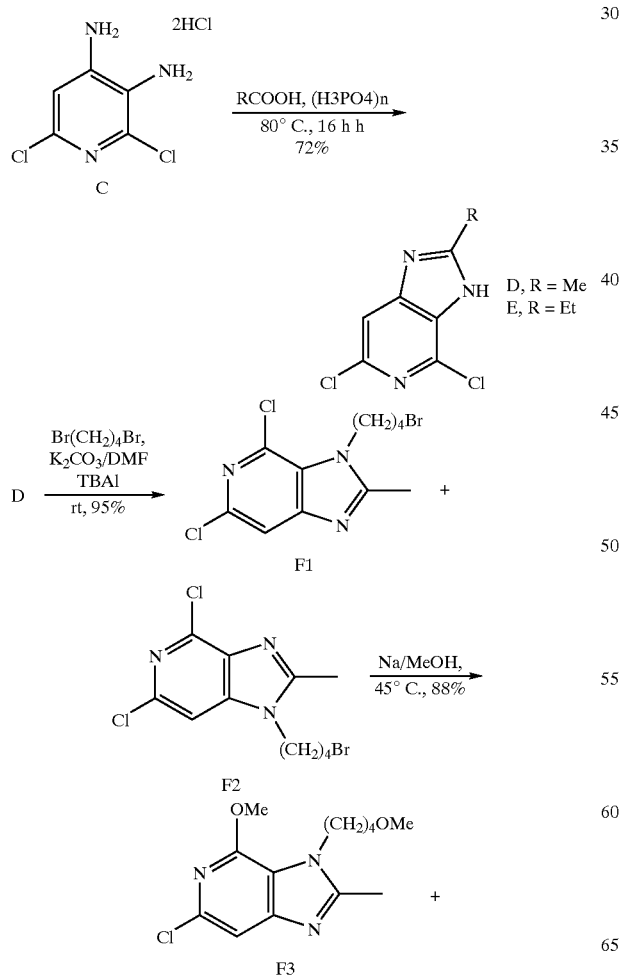

Scheme 4.
Synthesis of 7-alkoxyalkyl-2-amino-6-oxo-3-deazapurines.

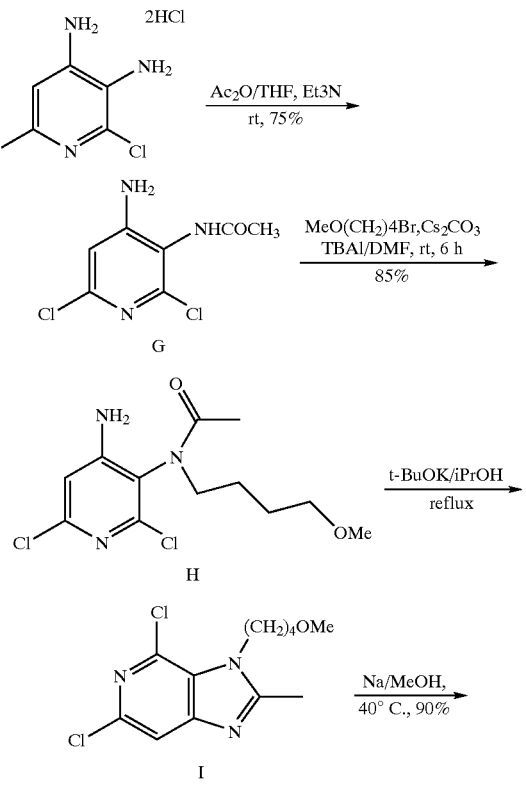

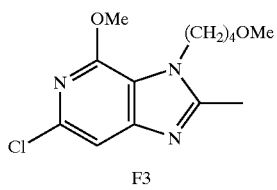

F3

The general method to prepare 3-deaza-8-azapurine compounds of the invention is summarized in Scheme 5.

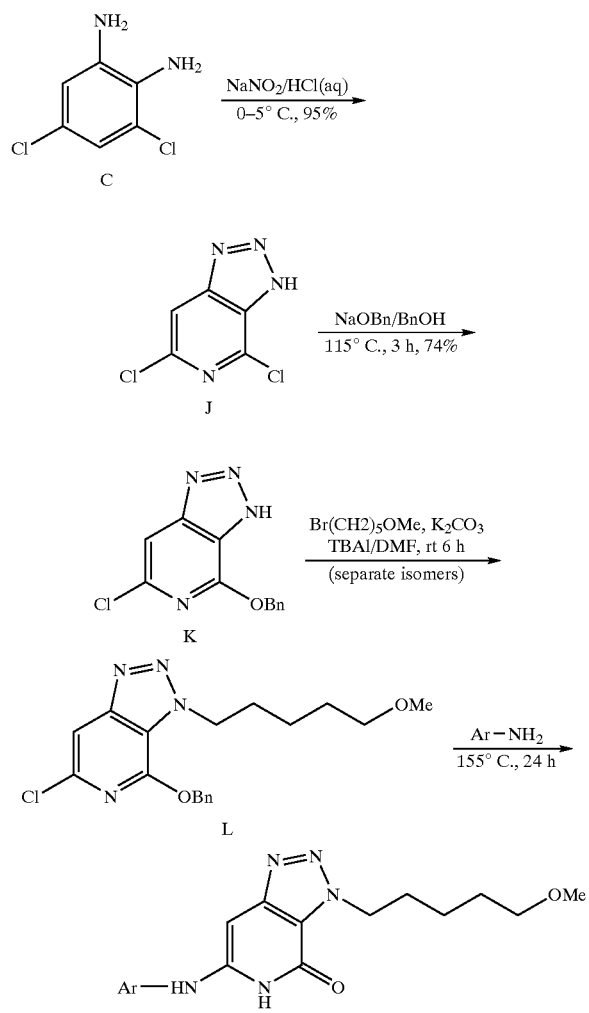

Purine compounds of the invention may be prepared by methods available in the literature, e.g. Xu et al., J. Med. Chem. 1995, 38, 49–57, Medveczky, et al., J. Med. Chem. 1995, 38, 1811–1819, and the identification of 7 and 9 isomers is routine (op. cit.). Scheme 6 exemplifies the general strategy for synthesis of these compounds with the examples of compounds 8 and 10.

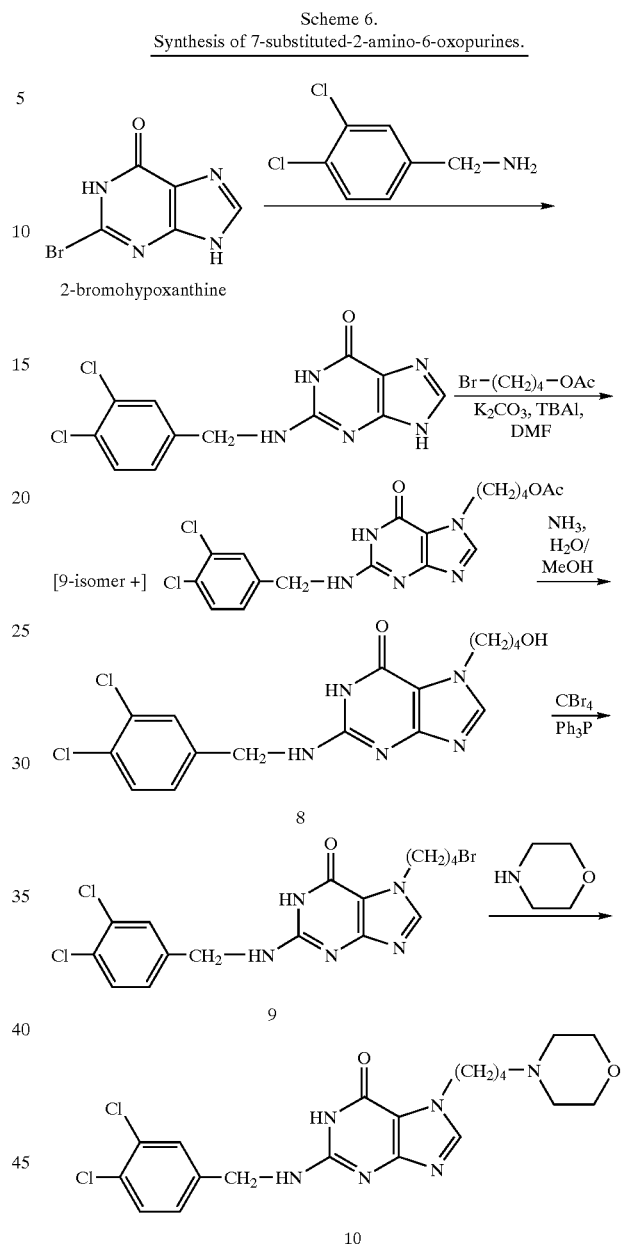

Representative Syntheses

6-Benzyloxy-2-chloroimidazo[4,5-c]pyridine (B). Powdered NaOH (2 g, 50 mmol) was added to a solution of 2,6-dichloroimidazo[4,5-c]pyridine (A) (3.0 g, 16 mmol) in benzyl alcohol (35 mL), and the mixture was stirred at 150° C. overnight. Most of the solvent was removed in vacuo, the residue mixed with water (20 mL), and the pH was adjusted to 7 using acetic acid. The mixture was extracted with $CHCl_3$ (10×50 mL), and the combined organic layer was washed with brine and concentrated to remove solvent. The residue was applied to a silica gel column and eluted with 2% MeOH in $CHCl_3$ to yield 3.8 g (89%) of product. $^1$H NMR (DMSO-$d_6$): δ 12.85 (1H, s, N—H), 8.25 (1H, s, 8-H), 7.50 (2H, m, Ar—H), 7.25 (3H, m, Ar—H), 7.20 (1H, s, 3-H), 5.50 (2H, s, $CH_2$).

3-Deaza Compounds 7- and 9-(ω-Bromoalkyl)-6-benzyloxy-2-chloro-3-deazapurines (B1, B2)—general method. $K_2CO_3$ (1.38 g, 10 mmol), Br(CH$_2$)$_n$Br (10 mmol) and tetrabutylammonium iodide (TBAI, 80 mg) were added to a solution of 6-benzyloxy-2-chloroimidazo[4,5-c]pyridine (B) (1.5 g, 6.0 mmol) in N,N-dimethylformamide (DMF) (25 mL). The reaction was stirred at rt overnight. The solvent was removed in vacuo, and the residue was applied to a silica gel column and eluted with 1.5% iPrOH in CH$_2$Cl$_2$ to yield 2.15 g of the mixture of 7 and 9 isomers in a ratio of about 2.5:1.

7- and 9-(4-Bromobutyl)-6-benzyloxy-2-chloro-3-deazapurines (B1, B2, n=4). $^1$H NMR (CDCl$_3$): δ 7.83 (0.71 H, s, 8-H of 7-isomer), 7.78 (0.29H, s, 8-H of 9-isomer), 7.57–7.28 (5H, m, Ar—H), 7.31 (0.71 H, s, 3-H of 7), 6.98 (0.29 H, s, 3-H of 9), 5.57 (0.29×2H, s, PhCH$_2$ of 9), 5.50 (0.71×2H, s, PhCH$_2$ of 7), 4.25 (0.71×2H, t, NCH$_2$ of 7), 4.10 (0.29×2H, t, NCH$_2$ of 9), 3.39 (0.29×2H, t, BrCH$_2$ of 9), 3.21 (0.71×2H, t, BrCH$_2$ of 7), 2.00–1.50 (2×2H, m, CH$_2$).

7- and 9-(5-Bromopentyl)-6-benzyloxy-2-chloro-3-deazapurines (B1, B2, n=5). $^1$H NMR (CDCl$_3$): δ 7.83 (0.71 H, s, 8-H of 7-isomer), 7.78 (0.29H, s, 8-H of 9-isomer), 7.57–7.28 (5H, m, Ar—H), 7.31 (0.71 H, s, 3-H of 7), 6.98 (0.29 H, s, 3-H of 9), 5.57 (0.29×2H, s, PhCH$_2$ of 9), 5.50 (0.71×2H, s, PhCH$_2$ of 7), 4.25 (0.71×2H, t, NCH$_2$ of 7), 4.10 (0.29×2H, t, NCH$_2$ of 9), 3.39 (0.29×2H, t, BrCH$_2$ of 9), 3.21 (0.71×2H , t, BrCH$_2$ of 7-isomer), 1.90–1.30 (3×2H, m, CH$_2$).

7- and 9-(ω-Methoxyalkyl)-6-benzyloxy-2-chloro-3-deazapurines (B3, B4)—general method. The mixture of bromoalkyl compounds B1 and B2 (10 mmol) was added to a solution of freshly prepared NaOMe (30 mmol) in MeOH, and the mixture was stirred at 45° C. for 16 h. The reaction was brought to rt, and ice-water (10 mL) was added. The pH was adjusted to 7 using acetic acid, the solvent was removed, and the residue was partitioned between water and CHCl$_3$ (3×100 mL). The combined organic layer was washed with brine and concentrated to remove solvent. The residue was applied to a silica gel column, and the 7 isomer B3 (6.5 mmol, 65%) eluted first in 1.5% iPrOH in CH$_2$Cl$_2$, and the 9 isomer B4 (2.5 mmol, 25%) eluted next in 3% iPrOH in CH$_2$Cl$_2$.

7-(4-Methoxybutyl)-6-benzyloxy-2-chloro-3-deazapurine (B3, n=4). $^1$H NMR (DMSO-d$_6$): δ 8.40 (1H, s, 8-H), 7.50 (2H, m, Ar—H), 7.35 (3H, m, Ar—H), 7.34 (1H, s, 3-H), 5.51 (2H, s, ArCH$_2$), 4.30 (2H, t, NCH$_2$), 3.18 (2H, t, OCH$_2$), 3.11 (3H, s, OC$_3$) 1.75, 1.30 (2×2H, m, CH$_2$).

7-(5-Methoxypentyl)-6-benzyloxy-2-chloro-3-deazapurine (B3, n=5). $^1$H NMR (DMSO-d$_6$): δ 8.40 (1H, s, 8-H), 7.50 (2H, m, Ar—H), 7.35 (3H, m, Ar—H), 7.34 (1H, s, 3-H), 5.51 (2H, s, ArCH$_2$), 4.25 (2H, t, NCH$_2$), 3.16 (2H, t, OCH$_2$), 3.12 (3H, s, OCH$_3$), 1.75, 1.40, 1.15 (3×2H, m, CH$_2$).

9-(4-Methoxybutyl)-6-benzyloxy-2-chloro-3-deazapurine (B4, n=4). $^1$H NMR (DMSO-d$_6$): δ 8.25 (1H, s, 8-H), 7.53 (2H, m, Ar—H), 7.52 (1H, s, 3-H), 7.35 (3H, m, Ar—H), 5.51 (2H, s, ArCH$_2$), 4.20 (2H, t, NCH$_2$), 3.30 (2H, t, OCH$_2$), 3.20 (3H, s, OCH$_3$), 1.80, 1.45 (2×2H, m, CH$_2$).

9-(5-Methoxypentyl)-6-benzyloxy-2-chloro-3-deazapurine (B4, n=5). $^1$H NMR (DMSO-d$_6$): δ 8.25 (1H, s, 8-H), 7.49 (2H, m, Ar—H), 7.48 (1H, s, 3-H), 7.35 (3H, m, Ar—H), 5.48 (2H, s, ArCH$_2$), 4.18 (2H, t, NCH$_2$), 3.25 (2H, t, OCH$_2$), 3.16 (3H, s, OCH$_3$), 1.75, 1.45, 1.20 (3×2H, m, CH$_2$).

7- and 9-(ω-Morpholinylalkyl)-6-benzyloxy-2-chloro-3-deazapurines (B5, B6)—general method. K$_2$CO$_3$ (138 mg, 1 mmol) and morpholine (87 mg, 1 mmol) were added to a solution of the bromoalkyl compounds B1 and B2 (0.43 mmol) in MeCN (15 mL). The mixture was stirred at rt overnight, the solvent was removed, and the residue was applied to a silica gel column. Elution with 3% MeOH in CHCl$_3$ yield product (0.43 mmol) as a mixture of two isomers.

7- and 9-(4-Morpholinylbutyl)-6-benzyloxy-2-chloro-3-deazapurines (B5, B6, n=4). $^1$H NMR (CDCl$_3$): δ 7.85 (0.71H, s, 8-H of 7-isomer), 7.78 (0.29 H, s, 8-H of 9-isomer), 7.55–7.20 (5H, m), 7.30 (0.71H, s, 3-H of 7), 7.00 (0.29H, s, 3-H of 9), 5.60 (0.29×2H, s, ArCH$_2$ of 9), 5.53 (0.71×2H, s, ArCH$_2$ of 7), 4.30 (0.71×2H, t, N–CH$_2$ of 7), 4.08 (0.29×2H, t, N–CH$_2$ of 9). 3.70–3.60 (4H, m, O—(CH$_2$)$_2$ of morpholine), 2.40–2.10 (6H, m, N–(CH$_2$)$_3$ of morpholine), 1.80, 1.30 (2×2H, m, CH$_2$).

7- and 9-(5-Morpholinylpentyl)-6-benzyloxy-2-chloro-3-deazapurines (B5, B6, n=5). $^1$H NMR (CDCl$_3$): δ 7.84 (0.71H, s, 8-H of 7-isomer), 7.79 (0.29 H, s, 8-H of 9-isomer), 7.59–7.30 (5H, m), 7.33 (0.71H, s, 3-H of 7), 6.99 (0.29H, s, 3-H of 9), 5.60 (0.29×2H, s, ArCH$_2$ of 9), 5.54 (0.71×2H, s, ArCH$_2$ of 7), 4.26 (0.71×2H, t, N–CH$_2$ of 7), 4.08 (0.29×2H, t, N–CH$_2$ of 9). 3.69–3.62 (4H, m, O(CH$_2$)$_2$ of morpholine), 2.40–2.12 (6H, m, N–(CH$_2$)$_3$ of morpholine), 1.80, 1.35, 1.12 (3×2H, m CH$_2$).

2-Amino-6-oxo-3-deazapurines—general procedure. The appropriate amine (4 eq) was mixed with 2-chloro-6-benzyloxy-3-deazapurine or the intermediates B3–B6 in a test tube, and the mixture was heated at 155° C. for 24 h under N$_2$. The tube was cooled to rt, and CHCl$_3$ (2 mL) was added. The solution was applied to a silica gel column, and product was eluted in a mixture of MeOH and CHCl$_3$.

2-(3,4-Dichlorobenzylamino)-6-oxo-3-deazapurine (1). Elution solvent 15% MeOH in CHCl$_3$, yield 40%. $^1$H NMR (DMSO-d$_6$): δ 12.00 (1H, s, 7-NH), 10.26 (1H, s, 1-NH), 7.68 (1H, s, 8-H), 7.60 (1H, d, Ar—H), 7.58 (1H, d, Ar—H), 7.32 (1H, dd, Ar—H), 6.08 (1H, t, ArNH), 5.22 (1H, s, 3-H), 4.30 (2H, d, ArCH$_2$).

2-(3,4-Dichlorobenzylamino)-6-oxo-7-(4-methoxybutyl)-3-deazapurine (2). Elution solvent 2% MeOH in CHCl$_3$, yield 72%. $^1$H NMR (DMSO-d$_6$): δ 10.42 (1H, s, 1-NH), 7.89 (1H, s, 8-H), 7.62 (1H, d, Ar—H), 7.61 (1H, d, Ar—H), 7.35 (1H, dd, Ar—H), 5.91(1H, t, Ar–NH), 5.31 (1H, s, 3-H), 4.30 (2H, d, ArCH$_2$), 4.22 (2H, t, N–CH$_2$), 3.25 (2H, t, O—CH$_2$), 3.16 (3H, s, OCH$_3$), 1.78, 1.40 (2×2H, m, CH$_2$).

2-(3,4-Dichlorobenzylamino)-6-oxo-7-(5-methoxypentyl)-3-deazapurine (3). Elution solvent 2% MeOH in CHCl$_3$, yield 71%. $^1$H NMR (DMSO-d$_6$): δ 10.25 (1H, s, 1-NH), 7.88 (1H, s, 8-H), 7.61(2H, m, Ar—H), 7.33 (1H, dd, Ar—H), 5.89 (1H, t, ArNH), 5.30 (1H, s, 3-H), 4.27 (2H, d, ArCH$_2$), 4.19 (2H, t, NCH$_2$), 3.22 (2H, t, OCH$_2$), 3.18 (3H, s, OCH$_3$), 1.72, 1.46, 1.19 (3×2H, m, CH$_2$).

2-(3-Ethyl-4-methylphenylamino)-6-oxo-7-(4-methoxybutyl)-3-deazapurine (15). Elution solvent 2% MeOH in CHCl$_3$, yield 62%. $^1$H NMR (CDCl$_3$): δ 11.55 (1H,s, 1-NH), 7.70 (1H, s, 8-H), 7.10(1H, d, Ar—H), 7.00 (1H, d, Ar—H), 6.90 (1H, dd, Ar—H), 6.30 (1H, s, Ar–NH), 6.25 (1H, s, 3-H), 4.35 (2H, t, NCH$_2$), 3.35 (2H, t, OCH$_2$), 3.25 (3H, s, OCH$_3$), 2.50 (2H, q, C–CH$_2$), 2.30 (3H, s, Ar–CH$_3$), 1.90, 1.50 (2×2H, m, CH$_2$), 1.15 (3H, t, C–CH$_3$).

2-(3-Ethyl-4-methylphenylamino)-6-oxo-7-(5-methoxypentyl)-3-deazapurine (17). Elution solvent 3% MeOH in CHCl$_3$, yield 59%. $^1$H NMR (DMSO-d$_6$): δ 11.02 (1H, s, 1-NH), 8.50 (1H, s, Ar–NH), 8.12 (1H, s, 8-H), 7.02 (1H, d, Ar—H), 6.90 (1H, d, Ar—H), 6.83 (1H, dd, Ar—H), 5.80 (1H, s, 3-H), 4.27 (2H, t, NCH$_2$), 3.26

(2H, t, OCH$_2$), 3.18 (3H, s, OCH$_3$), 2.46 (2H, q, CCH$_2$), 2.18 (3H, s, ArCH$_3$), 1.79, 1.48, 1.20 (3×2H, m, CH$_2$), 1.15 (3H, t, CCH$_3$).

2-(3-Ethyl-4-methylphenylamino)-6-oxo-7-(4-morpholinylbutyl)-3-deazapurine (16). Elution solvent 5% MeOH in CHCl$_3$, yield 68%. $^1$H NMR (CDCl$_3$): δ 10.80 (1H, s, 1-NH), 7.70 (1H, s, 8-H), 7.59 (1H, s, 2-NH), 7.03(1H, d, ArH), 7.00 (1H, d, Ar—H), 6.94 (1H, dd, Ar—H), 6.18 (1H, s, 3-H), 4.36 (2H, t, NCH$_2$), 3.88 (4H, m, O(CH$_2$)$_2$), 2.80–2.60 (6H, m, N(CH$_2$)$_3$ of morpholine), 2.55 (2H, q, CCH$_2$), 2.20 (3H, Ar–CH$_3$), 1.86, 1.65 (2×2H, m, CH$_2$), 1.18 (3H, t, CCH$_3$).

2-(3,4-Dichlorobenzylamino)-6-oxo-7-(4-morpholinylbutyl)-3-deazapurine (4). Elution solvent 5% MeOH in CHCl$_3$, yield 62%. $^1$H NMR (DMSO-d$_6$): δ 10.58 (1H, s, 1-NH), 7.90 (1H, s, 8-H), 7.45 (2H, m, Ar—H), 7.27(1H, dd, Ar—H), 6.15 (1H, t, 2-NH),5.26 (1H, s, 3-H), 4.25 (2H, d, ArCH$_2$), 4.20 (2H, t, NCH$_2$), 3.60 (4H, m, O(CH$_2$)$_2$), 2.95–2.60 (6H, m, N(CH$_2$)$_3$ of morpholine), 1.80, 1.50 (2×2H, m, CH$_2$).

2-(3,4-Dichlorobenzylamino)-6-oxo-9-(4-morpholinylbutyl)-3-deazapurine (24). Elution solvent 10% MeOH in CHCl$_3$, yield 53%. $^1$H NMR (DMSO-d$_6$): δ 10.25 (1H, s, 1-NH), 7.56 (2H, s, 8-H and Ar—H), 7.40 (1H, d, Ar—H), 7.21(1H, dd, Ar—H), 6.08 (1H, t, 2-NH), 5.22 (1H, s, 3-H), 4.25 (2H, d, ArCH$_2$), 3.85 (2H, t, NCH$_2$), 3.55 (4H, O(CH$_2$)$_2$), 2.35–2.15 (6H, m, N(CH$_2$)$_3$ of morpholine), 1.68, 1.38 (2×2H, m, CH$_2$).

2-(3,4-Dichlorobenzylamino)-6-oxo-7-(5-morpholinylpentyl)-3-deazapurine (5). Elution solvent 6% MeOH in CHCl$_3$, yield 61%. $^1$H NMR (CDCl3): δ 11.16 (1H, s, 1-NH), 7.58 (1H, s, 8-H), 7.42 (1H, d, Ar—H), 7.32 (1H, d, Ar—H), 7.18 (1H, dd, Ar—H), 6.25 (1H, t, 2-NH), 5.45 (1H, s, 3-H), 4.20 (4H, m, ArCH$_2$ and NCH$_2$), 3.75 (4H, m, O(CH$_2$)$_2$), 2.72–2.45 (6H, m, N(CH$_2$)$_3$ of morpholine, 1.80, 1.60, 1.25 (3×2H, m, CH$_2$).

8-Substituted-3-deaza Compounds 4,6-Dichloro-2-methylimidazo[4,5-c]pyridine (D). A solution of 3,4-diamino-2,6-dichloropyridine (510 mg, 2 mmol) and acetic acid (1 mL) in polyphosphoric acid (5 mL) was stirred at 80° C. for 16 h. The mixture was poured into ice-water (10 mL), the pH was adjusted to 8 with aq. NaOH, and the aqueous layer was extracted with ethyl acetate (3×50 mL). The organic layer was washed with brine and dried over Na$_2$SO$_4$. The solvent was removed, and the residue was applied to a silica gel column. Elution with 4% MeOH in CHCl$_3$ afforded the product (260 mg, 71%). $^1$H NMR (DMSO-d$_6$): δ 13.20 (1H, s, N—H ), 7.65 (1H, s, 3-H), 2.62 (3H, s, CH$_3$).

4,6-Dichloro-2-ethylimidazo[4,5-c]pyridine (E). The method for compound D using propionic acid gave the product in 62% yield. $^1$H NMR (DMSO-d$_6$): δ 13.20 (1H, s, N—H), 7.65 (1H, s), 2.80 (2H, q, CH$_2$), 1.25 (3H, t, CH$_3$).

7- and 9-(4-Bromobutyl)-2,6-dichloro-8-methyl-3-deazapurines (F1, F2). K$_2$CO$_3$ (276 g, 2 mmol), Br(CH$_2$)$_4$Br (3 mmol) and TBAI (30 mg) were added to a solution of compound D (1 mmol) in DMF (15 mL), and the mixture was stirred at rt overnight. The solvent was removed in vacuo, and the residue was applied to a silica gel column. Elution with 1.5% iPrOH in CH$_2$Cl$_2$ yielded 0.9 mmol of a mixture of 7 and 9 isomers in a ratio of 1:3. $^1$H NMR (CDCl$_3$): δ 7.49 (0.25 H, s, 3-H of 7-isomer), 7.19 (0.75H, s,3-H of 9-isomer), 4.42 (0.25×2H, t, NCH$_2$ of 7), 4.11 (0.75×2H, t, NCH$_2$ of 9), 3.84 (0.25×2H, t, BrCH$_2$ of 7), 3.42 (0.75×2H, t, BrCH$_2$ of 9), 2.65 (0.75× 3H, s, CH$_3$ of 7 ), 2.64 (0.25×3H, s, CH$_3$ of 9), 1.98 (4H, m, 2×CH$_2$).

7- and 9-(4-Methoxybutyl)-2-chloro-6-methoxy-8-methyl-3-deazapurines (F3, F4). A solution of F1 and F2 (0.6 mmol) in MeOH was added to a solution of freshly prepared NaOMe (3 mmol) in MeOH, and the mixture was stirred at 40° C. for 16 h. The solvent was removed in vacuo, and ice-water (10 mL) was added. The pH was adjusted to 7 using acetic acid, the mixture was partitioned between water and CHCl$_3$ (3×50 mL), and the combined organic layer was washed with brine and evaporated to dryness. The residue was applied to a silica gel column, and elution with 2.5% iPrOH in CH$_2$Cl$_2$ gave a mixture of two isomers in quantitative yield. $^1$H NMR (CDCl$_3$): δ 7.16 (0.25×1H, s, 3-H of 7-isomer), 6.80 (0.75×1H, 3-H of 9-isomer), 4.25 (0.25×2H, t, NCH$_2$ of 7), 4.11(0.75×3H, OCH$_3$ of 9), 4.09(0.25×3H, OCH$_3$ of 7), 4.05 (0.75×2H, NCH$_2$ of 9), 3.38 (2H, m, OCH$_2$ of both), 3.33 (0.75×3H, OCH$_3$ of 9), 3.31 (0.25×3H, OCH$_3$ of 7), 1.87, 1.58 (2×2H, m, CH$_2$).

2-(3,4-Dichlorobenzylamino)-6-oxo-7-(4-methoxybutyl)-8-methyl-3-deazapurine (6). 3,4-Dichlorobenzylamine (4 eq) was added to the F3 and F4 mixture in a test tube, and the mixture was heated at 155° C. for 24 h under N$_2$. The tube was cooled to rt, and CHCl$_3$ (2 mL) was added. The solution was applied to a silica gel column, and products were eluted in a mixture of MeOH and CHCl$_3$. Elution with 3% MeOH in CHCl$_3$ gave, after crystallization from diethyl ether/petroleum ether, compound 6 in 60% yield (based on F3). $^1$H NMR (CDCl$_3$): δ 12.45(1H, s, 1-NH), 7.45–7.32(2H, m, Ar—H), 7.12(1H, m, Ar—H), 5.50 (1H, s, 3-H), 5.08 (1H, t, 2-NH), 4.25 (2H, d, ArCH$_2$), 4.20 (2H, t, NCH$_2$), 3.30 (2H, t, OCH$_2$), 3.25 (3H, s, OCH$_3$), 2.45 (3H, s, 8-CH$_3$), 1.80, 1.55 (2×2H, m, CH$_2$). Continued elution with 15% MeOH in CHCl$_3$ gave, after crystallization from CHCl$_3$/MeOH, the 9-isomer 25 in 75% yield (based on F4). $^1$HNMR (CDCl$_3$): δ12.45(1H, s, 1-NH), 7.35–7.20(2H, m, Ar—H), 7.00 (1H, m, Ar—H), 5.25 (1H, s, 3H), 4.85 (1H, s, 2-NH), 4.20 (2H, d, ArCH$_2$), 3.66 (2H, t, NCH$_2$), 3.35 (2H, s, ArCH$_2$), 3.15 (5H, m, OCH$_2$+OCH$_3$), 2.32 (3H, s, 8-CH$_3$), 1.60, 1.40 (2×2H, m, CH$_2$).

3-Acetamido-4-amino-2,6-dichloropyridine (G). Acetic anhydride (1.50 g) and Et$_3$N (1.60 g) were added to a solution of 3,4-diamino-2,6-dichloropyridine dihydrochloride (628 mg, 2.5 mmol) in THF (15 mL). After stirring at rt overnight, the solvent was removed, and the residue was applied to a silica gel column. Elution with 5% MeOH in CHCl$_3$ yielded 415 mg (75%) of product. $^1$H NMR (DMSO-d$_6$): δ 9.15 (1H, s, AcNH), 6.55 (3H, s, NH$_2$ and 4-H), 1.98 (3H, s, CH$_3$CO).

3-[N-Acetyl-N-(4-methoxybutyl)amino]-4-amino-2,6-dichloropyridine (H). Cs$_2$CO$_3$ (650 mg, 2 mmol) and TBAI (74 mg, 0.2 mmol) were added to a solution of compound G (180 mg, 0.8 mmol) in DMF (15 mL). After stirring at rt for 10 min, Br(CH$_2$)$_4$OCH$_3$ (200 mg, 1.2 mmol) was added, and the mixture stirred for 6 h. The solvent was removed in vacuo, and the residue was applied to a silica gel column. Elution with 3% MeOH in CHCl$_3$ afforded 200 mg (75%) compound H as an oil. $^1$H NMR (CDCl$_3$): δ 6.76 (1H, s, 4-H), 5.15 (2H, s, NH$_2$), 3.65 (2H, t, NCH$_2$), 3.28 (2H, t, OCH$_2$), 3.24 (3H, s, OCH$_3$), 1.83 (3H, s, COCH$_3$), 1.60, 1.50 (2×2H, m, CH$_2$).

2,6-Dichloro-7-(4-methoxybutyl)-8-methyl-3-deazapurine (I). A solution of tBuOK (784 mg, 7 mmol) and compound H (200 mg, 0.6 mmol) in iPrOH (15 mL) was stirred under reflux for 2 h. The solvent was removed in vacuo, and water (30 mL) was added. The pH was adjusted to 7 using acetic acid, and the solution was extracted with CHCl$_3$. The organic layer was washed with brine and evaporated to afford compound I (200 mg, 95%). $^1$H NMR (CDCl$_3$): δ 7.12 (1H, s, 3-H), 4.24 (2H, t, NCH$_2$), 3.35 (2H, t, OCH$_2$), 3.31(3H, s, OCH$_3$), 2.56 (3H, s, 8-CH$_3$), 1.81, 1.61 (2×2H, m, CH$_2$).

7-(4-Methoxybutyl)-2-chloro-6-methoxy-8-methyl-3-deazapurine (F3). A solution of compound I in MeOH (3 mL) was added to freshly prepared NaOMe (3 mmol) in MeOH (15 mL) and the mixture was stirred at 40° C. for 6 h. The mixture was cooled to rt, and the solvent was removed. Ice water (10 mL) was added and the pH was adjusted to 7 using acetic acid. The solution was extracted with CHCl$_3$ and the organic layer dried over MgSO$_4$. The solution was concentrated and the residue applied to a silica gel column. Elution with 3% MeOH in CHCl$_3$ gave 178 mg (90%) of product. $^1$H NMR (CDCl$_3$): δ 7.16 (1H, s, 3-H), 4.24 (2H, t, NCH$_2$), 4.10 (3H, ring OCH$_3$), 3.38 (2H, m, O—CH$_2$), 3.30 (3H, side chain OCH$_3$), 1.85, 1.56 (2×2H, m, CH$_2$), identical with the F3 component of the F3/F4 mixture (see above).

3-Deaza-8-aza Compounds 4,6-Dichloro-1,2,3-triazolo[4,5-c]pyridine (J). Sodium nitrite (280 mg, 4 mmol) was added to a solution of compound C (1 g, 4 mmol) in 2N hydrochloric acid (2.5 mL) at 0° C., and stirred for 5 min. Water (2 mL) was added and the white precipitate was filtered and washed with ice-water and dried to afford compound J (780 mg, 95%). $^1$H NMR (DMSO-d$_6$): δ 8.10 (1H, s).

4-Benzyloxy-6-chloro-1,2,3-triazolo[4,5-c]pyridine (K). Sodium (230 mg) in benzyl alcohol (20 mL) was heated to 80° C. for 0.5 h (until sodium was completely reacted). The solution was cooled to rt, and compound J (500 mg, 2.7 mmol) was added. The dark solution was stirred for 3 h at 115° C. Most of the solvent was removed in vacuo, and water (80 mL) was added to the residue. The pH was adjusted to 7 using acetic acid, and the solution was extracted with CHCl$_3$ (6×100 mL). After evaporation of the solvent, the residue was applied to a silica gel column. Elution with 2% MeOH in CHCl$_3$ afforded product (508 mg, 74%). $^1$H NMR (DMSO-d$_6$): δ 7.55 (3H, m, 3-H, 2×Ar—H), 7.40 (3H, Ar—H).

3-(5-Bromopentyl)-4-benzyloxy-6-chloro-1,2,3-triazolo[4,5-c]pyridine (L). Alkylation was carried out as described for F1 and F2. Purification on a silica gel column in 1% iPrOH in CH$_2$Cl$_2$ afforded the product in 65% yield, and the 1 isomer in 25% yield. Compound L: $^1$H NMR (CDCl$_3$): δ 7.48 (1H, s, 3-H), 7.42 (2H, m, Ar—H), 7.36 (3H, m, Ar—H), 5.57 (2H, s, PhCH$_2$), 4.72(2H, t, NCH$_2$), 3.37 (2H, t, BrCH$_2$), 1.90 1.75, 1.38 (3×2H, m, CH$_2$).

3-(5-Methoxypentyl)-4-methoxy-6-chloro-1,2,3-triazolo[4,5-c]pyridine (M). Treatment of L with NaOMe in MeOH, as described for F3 and F4, gave, after silica gel chromatography in 1% iPrOH in CH$_2$Cl$_2$, 90% yield of product. $^1$H NMR (CDCl$_3$): δ7.45 (1H, s, 3-H), 4.76 (2H, t, NCH$_2$), 4.13 (3H, s, 6-OCH$_3$), 3.30 (2H, t, OCH$_2$), 3.28 (3H, s, OCH$_3$), 1.99, 1.60, 1.38 (3×2H, m, CH$_2$).

7-(5-Methoxypentyl)-2-(3,4-dichlorobenzyl)-3-deaza-8-aza-6-oxopurine (26). Fusion of compound M with 3,4-dichlorobenzylamine, as described for 6, and silica gel chromatography in 2% MeOH in CHCl$_3$ gave the product in 50% yield. $^1$H NMR (CDCl$_3$): δ 11.20 (1H, s, 1-NH), 7.45 (2H, m, Ar—H), 7.22 (1H, Ar—H), 5.72 (1H, s, 3-H), 4.72 (2H, t, NCH$_2$), 4.57 (1H, t, 2-NH), 4.34 (2H, d, PhCH$_2$), 3.30 (2H, t, OCH$_2$), 3.28 (3H, s, OCH$_3$), 1.98, 1.58, 1.32 (3×H, m, CH$_2$).

2,7-Disubstituted Purinies 7-(4-Acetoxybutyl)-2-(3,4-dichlorobenzylamino)-6-oxopurine (7). Potassium carbonate (400 mg, 2.9 mmol) and 4-bromobutyl acetate (520 mg, 2.67 mmol) were added to a solution of 2-(3,4-dichlorobenzylamino)-6-oxopurine (Nucl. Acids Res. 1990, 18, 7381–7387) (750 mg, 2.42 mmol) in DMF (20 ml). After stirring for 2 days at 45° C., the cooled mixture was poured into water (80 ml), and the solution was extracted with CHCl$_3$ (4×50 ml). The organic layer was washed with water (100 ml) and brine (100 ml) and dried over magnesium sulfate. The filtrate was concentrated in vacuo, and the residue was chromatographed on a silica gel column. Elution with 2% MeOH in CHCl$_3$ gave the 7-isomer 7 (255 mg, 25%), and elution with 2.5% gave the 9-isomer (640 mg, 62%). $^1$H NMR (DMSO-d$_6$): δ 1.50 (m, 2H, CH$_2$), 1.80 (m, 2H, CH$_2$), 1.97 (s, 3H, CH$_3$CO), 3.94 (t, 2H, CH$_2$), 4.15 (t, 2H, CH$_2$N), 4.45 (d, 2H, CH$_2$Ar), 6.60 (t, 1H, NH), 7.30 (d, 1H, Ar—H), 7.56 (m, 2H Ar—H), 7.90 (s, 1H, C$_8$-H) and 10.86 (s, 1H, NH).

7-(4-Hydroxybutyl)-2-(3,4-dichlorobenzylamino)-6-oxopurine (8). Aqueous ammonia (40%, 5 mL) was added to a suspension of 7 (230 mg, 0.54 mmol) in MeOH (15 mL). After stirring for 6 hours at rt, the clear solution was evaporated to dryness, and the residue was chromatographed on a silica gel column. Elution with 15% MeOH in CHCl$_3$ gave the product (187 mg, 90%). $^1$H NMR (DMSO-d$_6$): δ 1.32 (m, 2H, CH$_2$), 1.80 (m, 2H, CH$_2$), 3.35 (t, 2H, CH$_2$O), 4.16 (t, 2H, CH$_2$N), 4.39 (t, 1H, OH), 4.45 (d, 2H, CH$_2$Ar), 6.61 (t, 1H, NH), 7.30 (d, 1H, Ar—H), 7.62 (m, 2H, Ar—H), 7.90 (s, 1H, C$_8$-H) and 10.86 (s, 1 H, NH).

7-(4-Bromobutyl)-2-(3,4-dichlorobenzylamino)-6-oxopurine (9). Carbon tetrabromide (332 mg, 1 mmol) was added to a suspension of 8 (140 mg, 0.37 mmol) in MeCN (20 mL). The mixture was stirred for 5 min at 0° C., and triphenylphosphine (262 mg, 1 mmol) was added. After stirring at rt overnight, the solvent was removed, and the residue was chromatographed on a silica gel column. Elution with 2.5% MeOH in CHCl$_3$ gave the product (120 mg, 73%). $^1$H NMR (DMSO-d$_6$): δ 1.68 (m, 2H, CH$_2$), 1.85 (m, 2H, CH$_2$), 3.56 (t, 2H, CH$_2$I), 4.18 (t, 2H, CH$_2$N), 4.45 (d, 2H, CH$_2$Ar), 6.60 (t, 1H, NH), 7.31 (d, 1H, Ar—H), 7.57 (m, 2H, Ar—H), 7.91 (s, 1H, C$_8$-H) and 10.86 (s, 1H, NH).

7-[4-(N-Morpholinyl)butyl]-2-(3,4-dichlorobenzylamino)-6-oxopurine (10). Morpholine (0.5 ml) was added to a solution of 9 (59 mg) in MeCN (20 mL). After heating the mixture at reflux for 2 hours, the solvent was removed and the residue was chromatographed on a silica gel column. Elution with 15% MeOH in CHCl$_3$ gave the product (59.5 mg, 99%). $^1$H NMR (DMSO-d$_6$): δ 1.30 (m, 2H, CH$_2$), 1.75 (m, 2H, CH$_2$), 2.25 (m, 6H, morph), 3.45 (m, 4H, 2×CH$_2$), 4.15 (t, 2H, CH$_2$N), 4.45 (d, 2H, CH$_2$Ar), 6.60 (t, 1H, NH), 7.31 (d, 1H, Ar—H), 7.60 (m, 2H, Ar—H), 7.90 (s, 1H, C$_8$-H) and 10.80 (s, 1H, NH).

7-(5-Acetoxypentyl)-2-(3,4-dichlorobenzylamino)-6-oxopurine (11). As described for 7, the product was obtained in 24% yield and the 9 isomer in 59% yield. $^1$H NMR (DMSO-d$_6$): δ 1.25 (m, 2H, CH$_2$), 1.57 (m, 2H, CH$_2$), 1.75 (m, 2H, CH$_2$), 1.97 (s, 3H), CH$_3$CO), 3.95 (t, 2H, CH$_2$), 4.18 (t, 2H, CH$_2$N) 4.50 (d, 2H, CH$_2$Ar), 6.65 (t,1H, NH), 7.35 (d, 1H, Ar—H), 7.60 (m, 2H, Ar—H), 7.96 (s, 1H, C$_8$-H) and 10.91 (s, 1H, NH).

7-(5-Hydroxypentyl)-2-(3,4-dichlorobenzylamino)-6-oxopurine (12). As described for 8, the product was obtained in 94% yield. $^1$H NMR (DMSO-d$_6$): δ 1.23 (m, 2H, CH$_2$), 1.40 (m, 2H, CH$_2$), 1.78 (m, 2H, CH$_2$), 3.35 (t, 2H, CH$_2$O), 4.19 (t, 2H, CH$_2$N), 4.36 (t, 1H, OH), 4.50 (d, 2H, CH$_2$Ar), 6.60 (t, 1H, NH), 7.32 (d, 1H, Ar—H), 7.57 (m, 2H, Ar—H), 7.91 (s, 1H, C$_8$–H) and 10.89 (s, 1H, NH).

7-(5-Iodopentyl)-2-(3,4-dichlorobenzylamino)-6-oxopurine (13). Treatment of 12 with trimethylsilyl iodide in CHCl$_3$, as described for 21, gave the product in 88% yield. $^1$H NMR (DMSO-d$_6$): δ 1.29 (m, 2H, CH$_2$), 1.76 (m, 4H, 2×CH$_2$), 3.28 (t, 2H, CH$_2$I), 4.20 (t, 2H, CH$_2$N), 4.50 (d, 2H, CH$_2$Ar), 6.62 (t, 1H, NH), 7.32 (d, 1H, Ar—H), 7.58 (m, 2H, Ar—H), 7.95 (s, 1H, C$_8$–H) and 10.85 (s, 1H, NH).

7- and 9-(4-Acetoxybutyl)-2-(3-ethyl-4-methylphenylamino)-6-chloropurines. Potassium carbonate (1.5 g, 11 mmol) and 4-bromobutyl acetate (3 g, 15.4 mmol) were added to a solution of 2-(3-ethyl-4-methylphenylamino)-6-chloropurine (J. Med. Chem. 1988, 31, 1496–1501) (1.8 g, 6.26 mmol) in MeCN (80 mL). After 4 h at reflux, the solvent was removed in vacuo, and the residue was chromatographed on a silica gel column. Chloroform eluted the 9 isomer (1.65 g, 65%), and 5% MeOH in CHCl$_3$ eluted the 7-isomer (378 mg, 15%). 7-isomer: $^1$H NMR (DMSO-d$_6$): δ 1.15 (t, 3H, CH$_3$) 1.57 (m, 2H, CH$_2$), 1.84 (m, 2H, CH$_2$), 2.26 (s, 3H, CH$_3$CO), 2.55 (q, 2H, CH$_2$), 3.98 (t, 2H, CH$_2$), 4.35 (t, 2H, CH$_2$N), 7.05 (d, 1H, ArH), 7.52 (d, 1H, ArH), 7.58 (dd, 1H, ArH), 8.56 (s, 1H, C$_8$–H) and 9.55 (s, 1H, NH).

7-(4-Hydroxybutyl)-2-(3-ethyl-4-methylphenylamino)-6-oxopurine (18). A solution of 7-(4-acetoxybutyl)-2-(3-ethyl-4-methylphenylamino)-6-chloropurine (50 mg, 0.125 mmol) in MeOH (3 mL) was added to aqueous NaOH (0.5N, 20 mL). After reflux for 2 days, the solvent was removed in vacuo, and the residue was chromatographed on a silica gel column. Elution with 7% MeOH in CHCl$_3$ gave the product (45 mg, 99%). $^1$H NMR (DMSO-d$_6$): δ 1.13 (t, 3H, CH$_3$), 1.30 (m, 2H, CH$_2$), 1.78 (m, 2H, CH$_2$), 2.18 (s, 3H, CH$_3$), 2.55 (q, 2H, CH$_2$), 3.32 (t, 2H, CH$_2$), 4.18 (t, 2H, CH$_2$N), 4.36 (t, 1H, OH), 7.05 (d, 1H, ArH), 7.28 (d, 1H, ArH), 7.45 (dd, 1H, ArH), 8.00 (s, 1H, C$_8$–H), 8.33 (s, 1H, NH) and 10.55 (s, 1H, NH).

7-(5-Acetoxypentyl)-2-(3-ethyl-4-methylphenylamino)-6-oxopurine (19). As described for the acetoxybutyl analogs, the product was obtained in 22% yield, and the 9 isomer in 53% yield. 19: $^1$H NMR (DMSO-d$_6$): δ 1.08 (t, 3H, CH$_3$), 1.20 (m, 2H, CH$_2$), 1.59 (m, 2H, CH$_2$), 1.84 (m, 2H, CH$_2$), 2.01 (s, 3H, CH$_3$CO$_2$), 2.14 (s, 3H, ArCH$_3$), 2.56 (q, 2H, ArCH$_2$), 3.92 (t, 2H, CH$_2$O), 4.18 (t, 2H, CH$_2$N) 7.02 (d, 1H, Ar—H), 7.24 (s,1H, Ar—H), 7.45 (d, 1H, Ar—H), 7.93 (s, 1H, C$_8$–H), 8.36 (s, 1H, NH) and 10.62 (s, 1H, NH).

7-(5-Hydroxypentyl)-2-(3-ethyl-4-methylphenylamino)-6-oxopurine (20). As described for 8, the product was obtained in 94% yield. $^1$H NMR (DMSO-d$_6$): δ 1.23 (m, 2H, CH$_2$), 1.40 (m, 2H, CH$_2$), 1.78 (m, 2H, CH$_2$), 3.35 (t, 2H, CH$_2$O), 4.19 (t, 2H, CH$_2$N), 4.36 (t, 1H, OH), 4.50 (d, 2H, CH$_2$Ar), 6.60 (t, 1H, NH), 7.32 (d, 1H, Ar—H), 7.57 (m, 2H, Ar—H), 7.91 (s, 1H, C$_8$–H) and 10.89 (s, 1H, NH).

7-(5-Iodopentyl)-2-(3-ethyl-4-methylphenylamino)-6-oxopurine (21). Iodotrimethylsilane (8.5 g, 42.5 mmol) was added to a stirred solution of 20 (5 g, 14.1 mmol) in dry CHCl$_3$ (100 mL). The reaction mixture was stirred at reflux overnight until disappearance of starting material (TLC). MeOH and sodium sulfite were added to the brown-purple solution, and, after stirring at rt for 10 min, the mixture was filtered and the solvent was removed. The residue was applied to a silica gel column and eluted with 1–2% MeOH in CHCl$_3$ to give 5.5 g (85% yield) of product. $^1$H NMR (DMSO-d$_6$): δ 1.08 (t, 3H, CH$_3$), 1.22 (m, 2H, CH$_2$), 1.76 (m, 4H, 2×CH$_2$), 2.15 (s, 3H, CH$_3$Ar), 2.56 (q, 2H, ArCH$_2$), 3.24 (t, 2H, CH$_2$I), 4.16 (t, 2H, CH$_2$N), 7.03 (d, 1H, Ar—H),7.24 (s, 1H, Ar—H), 7.45 (d, 1H, Ar—H), 8.02 (s, 1H, C$_8$-H), 8.35 (s, 1H, NH) and 10.62 (s, 1H, NH).

7-(5-Methoxypentyl)-2-(3-ethyl-4-methylphenylamino)-6-oxopurine (22). Compound 21 was heated in a solution of NaOMe in MeOH at 55° C. for 24 h. Solvent was removed, and the residue was dissolved in water and extracted with CH$_2$Cl$_2$. The organic layer was evaporated and the residue applied to a silica gel column. Elution with 1% MeOH in CHCl$_3$ gave the product in 77% yield. $^1$H NMR (DMSO-d$_6$): δ 1.10 (t, 3H, CH$_3$), 1.17 (m, 2H, CH$_2$), 1.52, 1.80 (m, 2H, 2×CH$_2$), 2.12 (s, 3H, CH$_3$Ar), 2.56 (q, 2H, ArCH$_2$), 3.13 (s, 3H, OCH$_3$), 3.22 (t, 2H, OCH$_2$), 4.14 (t, 2H, CH$_2$N), 7.03 (d, 1H, Ar—H), 7.24 (s, 1H, Ar—H), 7.45 (d, 1H, Ar—H), 8.02 (s, 1H, C$_8$–H), 8.28 (s, 1H, NH) and 10.62 (s, 1H, NH).

7-{5-[4-hydroxy-4-(3-trifluoromethyl-4-chlorophenyl)piperidyl]pentyl}-2-(3-ethyl-4-methylphenylamino)-6-oxopurine (23). Compound 21, potassium carbonate and 4-hydroxy-4-(3-chloro-4-trifluoromethylphenyl)piperidine were stirred in DMF at rt for 48 h. The solvent was removed in vacuo, and the residue was applied to a silica gel column. Elution with 10% MeOH in CHCl$_3$ gave the product in 51% yield. $^1$H NMR (DMSO-d$_6$): δ 10.71 (bd s, 1H, 1-H), 8.67 (s, 1H, 2NH), 8.04 (s, 1H, 8-H), 7.95 (s, 1H, Ar-b-2-H), 7.70 (m, 2H, Ar-b-5,6-H), 7.48 (dd, 1H, Ar-a-6-H), 7.30 (d, 1H, Ar-a-2-H), 7.07 (d, 1H, Ar-a-5-H), 5.41(bd s, 1H, 4-OH), 4.24(t, 2H, 7-NCH$_2$), 3.34 (t, 2H, pip-NCH$_2$), 2.61 (q, 2H, Ar-a-CCH$_2$), 2.27 (s, 3H, Ar-a-CH$_3$), 1.86 (m, 2H, CH$_2$), 1.66 (m, 2H, CH$_2$), 1.15(t, Ar-a-CCH$_3$).

Identification of Isomers

Alkylation of 3-deazapurines gave two isomeric products, tentatively identified as 7 and 9 alkylated products. Two dimensional NOESY (nuclear Overhauser enhancement spectroscopy) NMR experiments were conducted to assign the correct structures in the isomer pairs B3 and B4, 4 and 24, and 6 and 25. Proton-proton NOESY spectra of compounds B4, 24 and 25 showed crosspeaks between the NCH$_2$ and 3-H resonances, indicating that they were 9-alkylated isomers. These crosspeaks were absent in B3, 4 and 6 indicating that they were 7-alkylated isomers. In addition, B3 showed a crosspeak between the NCH$_2$ and benzyloxy CH$_2$ resonances, consistent with the 7-alkylated product. Definite proof that 6 was the 7-alkylated isomer was obtained by selective synthesis of that compound (Scheme 4). The product was identical to the isomer identified as the 7-alkylated product from synthesis according to Scheme 3.

Water Solubility

Certain of the compounds described herein have increased water solubility; derivatives with amine or carboxylic acid sidechains can form salts, such as with inorganic or organic acids, or with alkali metal or organic bases, respectively, thus greatly increasing their solubilities. The improved water solubilities are a distinct advantage in formulation and in dosing of animals for testing, and for ultimate therapeutic use in humans. For example, the compounds of this invention may contain functional groups such as secondary or tertiary amines or carboxylic acids that increase the water solubility of the compounds, facilitating their bioavailability, absorption, and distribution in humans and animals, without interfering with their inhibition of growth of Gram-positive and Gram-negative bacteria and mycoplasma spp.

Compound Efficacy

The ability of a test compound to inhibit the activity of DNA pol IIIC or pol IIIE enzymes can be tested by using a DNA polymerase assay as described, for example, in Barnes and Brown, Nucl. Acids Res. 1979, 6, 1203–1219; Trantolo et al., J. Med. Chem. 1986, 29, 676–681; Mills et al., J. Bacteriol. 1977, 132, 641–649; Low et al., J. Biol. Chem. 1976, 251, 1311–1325. This rapid screening method can use natural or recombinant DNA pol III enzymes in a standard DNA polymerase activity assay. By including a test compound in a side-by-side assay with a control, the effect of the test compound on polymerase activity can be assessed. Test compounds with an appropriate level of inhibition of the natural or recombinant bacterial DNA polymerase III are good candidate therapeutics for further evaluation.

Antimicrobial efficacy may be determined by standard methods of microbial culture in growth medium or on plates of agar supplemented with appropriate growth media. For example, microbes, e.g., mycoplasmata or Gram-positive or Gram-negative bacteria, are grown in the presence of serial dilutions of compounds in an appropriate vehicle, and, after a suitable period of growth, the microbial density is measured by visual or instrumental means. The concentration of compound at which no growth occurs is the minimum inhibitory concentration (MIC) of the compound. Test compounds with an appropriate level of growth inhibition are good candidate therapeutics for further evaluation.

Toxicity

The low toxicity of the compounds of the invention to mammals and other animals endows this class of agents with the characteristics required of Gram-positive- and Gram-negative- and mycoplasma-specific therapeutic antimicrobials. Since the compounds target essential enzymes in DNA replication that have not previously been a target for any marketed antibiotic, development of drug resistance will be minimized. The compounds can be used to circumvent the natural and acquired resistance of pathogenic Gram-positive and Gram-negative bacteria and mycoplasmata to conventional antimicrobials without harmful effects to the infected animal.

The toxicity of the compounds toward mammalian cells can be evaluated according to standard methods known to those skilled in the art (see, e.g., Gootz, Clin. Microbiol. Rev. 1990, 3, 13–31). The toxic concentration (or "$IC_{50}$") can be determined by using protocols well known in the field of pharmacology. A suitable range of $IC_{50}$ values for a compound to be considered for further therapeutic evaluation will be greater than the MIC in bacterial cultures, i.e., the therapeutic index should be greater than 10.

Therapeutic Administration of Compounds

The compounds described herein are useful for the treatment of microbial infections in animals, e.g., humans, caused by mycoplasmata, or Gram-positive and Gram-negative bacteria, including strains resistant to common antibiotic drugs. The compounds are also useful for the treatment of mycoplasmal infections in animals, e.g., humans, caused by various species of the genera *Mycoplasma* and *Ureaplasma*. They are also useful for the treatment of related Gram-positive and Gram-negative bacterial infections and mycoplasmal infections in animals such as pigs, cows, horses, goats, chickens, turkeys, sheep, rats, mice, and rabbits, and for eliminating or avoiding bacterial or mycoplasmal infections of eukaryotic cell cultures or other media, e.g., foods, cosmetics, medical devices, and hospital supplies.

The compounds of the invention can be formulated for pharmaceutical, veterinary, and tissue culture use, optionally together with an acceptable diluent, carrier, or excipient and/or in unit dosage form. In using the compounds of the invention, conventional pharmaceutical, veterinary, or culture practice can be employed to provide suitable formulations or compositions, all of which are encompassed by the pharmaceutical compositions of this invention.

For human or animal use, the formulations of this invention can be administered by parenteral administration, for example, intravenous, subcutaneous, intramuscular, intraorbital, ophthalmic, intraventricular, intracranial, intracapsular, intraspinal, intracisternal, or intraperitoneal administration, or by intranasal, aerosol, scarification, oral, buccal, rectal, vaginal, or topical administration. The formulations of this invention may also be administered by the use of surgical implants which release the compounds of the invention, either as a bolus or slowly over a pre-selected period of time.

Without limitation, parenteral formulations can be, for example, in the form of liquid solutions or suspensions; for oral administration, formulations can be, for example, in the form of tablets, capsules, liquid solutions and suspensions (wherein such solutions and suspensions are particularly for formulations intended for pediatric use); and for intranasal administration, the formulations can be, for example, in the form of powders, nasal drops, or aerosols. Other suitable formulations for parenteral, oral or intranasal delivery of the compounds of this invention will be well known to those of ordinary skill in the art.

Methods well known in the art for making formulations can be found in, for example, "Remington's Pharmaceutical Sciences." Formulations for parenteral administration may contain as excipients sterile water or saline, ethanol, propylene glycol, polyalkylene glycols such as polyethylene glycol, oils of vegetable origin, hydrogenated naphthalenes, or biocompatible, biodegradable lactide polymers. Polyoxyethylene-polyoxypropylene copolymers can be used to control the release of the present compounds. Other potentially useful parenteral delivery systems for the compounds of the invention include ethylene-vinyl acetate copolymer particles, osmotic pumps, implantable infusion systems, and liposomes. Formulations for inhalation may contain lactose as an excipient, or can be aqueous solutions containing, for example, polyoxyethylene-9-lauryl ether, glycocholate and deoxycholate, or can be oily solutions for administration in the form of nasal drops, or can be gels to be applied intranasally. Formulations for parenteral administration may also include glycocholate for buccal administration, methoxysalicylate for rectal administration, or citric acid for vaginal administration.

The concentration of the compound in the formulations of the invention will vary depending upon a number of factors, including the dosage to be administered, and the route of administration. In general, the compounds of the invention can be provided in an aqueous physiological buffer solution containing about 0.1 to 10% w/v compound for parenteral administration. General dose ranges are from about 0.01 mg/kg to about 1 g/kg of body weight per day, e.g., from about 0.01 mg/kg to 100 mg/kg of body weight per day. The dosage to be administered depends upon the type and extent of progression of the infection being addressed, the overall health of the patient, and the route of administration. For topical and oral administration, formulations and dosages can be similar to those used for other antibiotic drugs, e.g., erythromycin.

In one embodiment, a compound or composition of the invention is administered to an animal (e.g., swine, chicken, or other commercially relevant livestock) or to a human patient that has been diagnosed with a mycoplasmal or Gram-positive or Gram-negative bacterial infection. The compounds can also be administered to the animal or human to inhibit or reduce the likelihood of a mycoplasmal or Gram-positive or Gram-negative bacterial infection, particularly in an animal or human susceptible to such infections (including, without limitation, a human patient who is immunodeficient or immunocompromised or one who has recently undergone a medical procedure). In other embodiments, cultured eukaryotic cells, either those that have mycoplasmal or Gram positive or Gram-negative bacterial infections, are treated with the new compositions, or the compositions are added to inhibit or reduce the likelihood of such infections (e.g., prophylactic treatment). The compounds of the invention may also be used the prevent bacterial growth in food products, cosmetics, and medical supplies, and on surfaces.

The compounds can be administered both prophylactically and after infection has occurred. Prophylaxis can be most appropriate for immunocompromised animals and human patients and for animals and patients following surgery or dental procedures. This list of relevant conditions for application of the methods of the invention is not intended to be limiting, and any appropriate infection responsive to the compounds can be treated using the methods and/or compounds described herein.

The compounds may also be used to treat or coat media or surfaces to prevent or reduce the extent of microbial growth. For example, the compounds of the invention can be mixed with eukaryotic culture media (e.g., solid or liquid media) in order to prevent mycoplasmal or Gram-positive or Gram-negative bacterial growth. In addition, the compounds of the invention may be used in disinfectant formulations for treating surfaces, e.g., a liquid formulation for cleaning and disinfecting surfaces, such as those in kitchens, bathrooms, hospitals, or other areas of medical treatment or potential microbial growth. Medical devices and other surfaces can also be treated or coated with compounds of the invention in order to control microbial growth. Medical devices include those that are wholly or partially implanted in an animal and those external to an animal. Examples of medical devices include, without limitation, catheters, dialysis pumps, blood collection equipment, stents, and drug delivery devices. Standard formulations for the use of the compounds of the invention for surface treatments or in coatings are known to those skilled in the art.

EXAMPLES

The following specific examples are to be construed as merely illustrative, and not limitative of the remainder of the disclosure in any way.

Example 1

Enzyme Assays and Determination of Inhibitor $K_i$ Values

DNA pol III activity was assayed as described in Barnes et al., Nucl. Acids Res. 1979, 6, 1203–1219, using activated "nicked" calf-thymus DNA as template:primer, 10 pM [$^3$H-methyl]-dTTP as the labelled dNTP substrate, and dATP, dCTP, and dGTP at 25 $\mu$M each.

Inhibitory activity of the compounds was determined by measuring the ability of the agent to inhibit enzyme-catalyzed incorporation of [$^3$H]-dTMP into nicked calf thymus DNA in the absence of the competitor dGTP ("truncated assay", see Wright and Brown, Biochim. Biophys. Acta 1976, 432, 37–48). Purified pol IIIC or pol IIIE was added to a buffered solution containing $Mg^{2+}$, DTT, glycerol, nicked calf thymus DNA, saturating concentrations of dATP, dCTP, dTTP and [$^3$H]-dTTP. Reaction mixtures were incubated at 30° C. for 10 min, quenched and filtered, and radioactivity in the acid-insoluble material measured by scintillation counting. Experiments were done in triplicate. Inhibitors were assayed by addition of several dilutions of a stock solution of inhibitor (DMSO or water, depending on solubility) before enzyme addition. Typically compounds were tested at five concentrations to estimate the $K_i$ value. The truncated assay, i.e., exclusion of the competitive substrate dGTP allows for the direct determination of apparent inhibitor constants ($K_i$) in this assay system. The typical range of $K_i$ values for compounds of the invention was 0.01–0.5 $\mu$M.

Example 2

Inhibition of Bacterial Growth and Determination of Minimum Inhibitory Concentration (MIC) Values Each compound was assayed against a panel of Gram-positive *Bacilli, Enterococci,* and *Staphylococci,* and Gram-negative *Escherichia coli,* grown in appropriate plate media solidified with 1.3% agar-agar. Stock solutions of the compounds in DMSO or water, depending on solubility, were added to sterile medium at a temperature of 60° C. This stock mixture was diluted with drug-free medium and used to make a series of Petri plates containing inhibitor in a series of two-fold serial dilutions, from about 80 to 0.0625 $\mu$g/mL. One tenth mL of diluted bacteria containing 500–1000 colony-forming units (CFU) were plated and spread, and the plates were incubated at 37° C. for 24 hours. MIC (minimum inhibitory concentration) was equivalent to the lowest concentration at which growth, i.e. colony formation, was not observed. The typical range of MIC values for compounds of the invention was 0.1–40 $\mu$g/ml.

Example 3

Biological Activity

Table 1 summarizes the DNA polymerase inhibition and antimicrobial activity of representative compounds of the invention. The compounds are highly active DNA polymerase inhibitors and have antimicrobial activity. The phenylamino compounds also selectively inhibit pol IIIC, while the benzylamino compounds inhibit both pol IIIC and pol IIIE.

Example 4

Cell Permeability

Table 2 summarizes the results of cell membrane permeability assays of representative compounds of the invention. The assay utilizes CaCo$_2$ cell culture monolayers, described by Artursson and Kalsson, Biochem. Biophys. Res. Commun. 1991, 175, 880–885, in which permeability values P are correlated with extent of oral absorption in humans. Results for reference compounds for high oral absorption (propranolol) and low oral absorption (ranitidine) are included. The 3-deazapurine compounds 17 and 3 have P values comparable to that of propranolol.

TABLE 2

Cell permeability (P) of compounds of the invention.

| Cpd | Acronym | P × 10⁻⁶ (cm/s) |
|---|---|---|
| 17 | 7-MPn-3-deazaEMPG | 39.6 |
| 3 | 7-MPn-3deazaDCBG | 13.8 |
| 20 | 7-HPn-EMPG | 0.62 |
| 19 | 7-AcOPn-EMPG | 0.58 |
| 18 | 7-HB-EMPG | 0.56 |
| 10 | 7-MorB-DCBG.HCl | 0.01 |
|  | Propranolol | 19.3 |
|  | Ranitidine | 0.27 |

Other Embodiments

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and not intended to be limiting. A number of embodiments of the invention have been described. Nevertheless, it will be understood that one skilled in the art could make various modifications without departing from the spirit and scope of the invention. Accordingly, other embodiments are within the scope of the invention.

Other embodiments are in the claims.

What is claimed is:

1. A compound having the formula

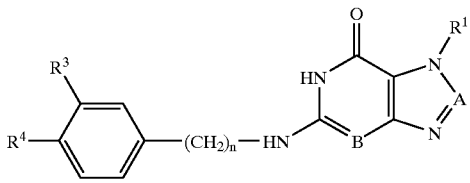

or a pharm,aceutically acceptable salt thereof, wherein A is $CR^2$ and B is N, in which $R^2$ is H, $C_{1-6}$ alkyl, vinyl, allyl, ethynyl, halo, $NH_2$, OH, SH, $OR^{29}$, $SR^{30}$, $NR^{31}R^{32}$, wherein $R^{29}$–$R^{32}$ are, independently, H or $C_{1-6}$ alkyl;

wherein n is 0–3;

wherein $R^3$ is H, lower ($C_{1-3}$) alkyl, lower ($C_{1-3}$) polyfluoroalkyl, trifluoromethoxy or halo, $R^4$ is H, methyl, ethyl, lower ($C_{1-3}$) polyfluoroalkyl, trifluoromethoxy or halo, or $R^3$ and $R^4$ are together —(CH$_2$)$_3$—;

wherein $R^1$ is $(CH_2)_m$—{$(G)_o$—$(CH_2)_p$}$_q$—L, in which G is $CH_2$, CH=CH, C≡C, CO, O, S, $NR^5$, where $R^5$ is H or $C_{1-6}$ alkyl, $CHR^6$, where $R^6$ is OH or $C_{1-6}$ alkyl, $CH(CR^7R^8)$, where each of $R^7$ and $R^8$ is, independently, H, halo, or $C_{1-6}$ alkyl, OCO, $CONR^9$, $NR^{10}CO$, where each of $R^9$ and $R^{10}$ is, independently, H or $C_{1-6}$ alkyl, $SO_2NH$, or $NHSO_2$;

in which L is H, halo, substituted or unsubstituted $C_{1-0}$ alkyl, substituted or unsubstituted $C_{3-8}$ cycloalkyl, substituted or unsubstituted $C_{6-14}$ aryl, substituted or unsubstituted $C_{5-10}$ heteroaryl, a substituted or unsubstituted 5–8 membered non-aromatic heterocycle, $NH_2$, CN, $OR^{11}$, $SR^{12}$, $COR^{13}$, $OCOR^{14}$, $NR^{15}(CO)R^{16}$, $NR^{17}R^{18}$, $NR^{19}(CO)NHR^{20}$, $CH(CO_2R^{21})_2$, $CO_2R^{22}$, $NHSO_2R^{23}$, $CONR^{24}R^{25}$, $CH_2COR^{26}$, $S(O)R^{27}$ or $S(O_2)R^{28}$ in which each of $R^{11}$–$R^{28}$ is, independently, H, substituted or unsubstituted $C_{1-6}$ alkyl, substituted or unsubstituted $C_{3-8}$ cycloalkyl, substituted or unsubstituted $C_{6-14}$ aryl, substituted or unsubstituted $C_{7-20}$ arylalkyl, substituted or unsubstituted $C_{7-20}$ alkylaryl, or substituted or unsubstituted $C_{5-12}$ heteroaryl; in which m is 1–4, o is 0–4, p is 0–4, and q is 0–4.

2. The compound of claim 1 in which n is 1, and $R^3$ and $R^4$ are, independently, fluoro, chloro, bromo, trifluoromethyl, or trifluoromethoxy.

3. The compound of claim 2 in which $R^1$ is 4-halobutyl, 4-hydroxybutyl, 4-acetoxybutyl, 4-methoxybutyl, 4-(N-morpholinyl)butyl, 4-(N-piperidinyl)butyl, 4-(N-piperazinyl)butyl, 5-methoxypentyl, 5-ethoxypentyl, 5-propoxypentyl, 5-methylthiopentyl, 5-methylsulfoxylpentyl, or 5-methylsulfonylpentyl.

4. The compound of claim 3, wherein said compound is selected from the group consisting of:

2-(3,4-dichlorobenzylamino)-7-(4-hydroxybutyl)-6-oxopurine, 2-(3,4-dichlorobenzylamino)-7-(4-acetoxybutyl)-6-oxopurine, 2-(3,4-dichlorobenzylamino)-7-(4-methoxybutyl)-6-oxopurine, 2-(3,4-dichlorobenzylamino)-7-(4-bromobutyl)-6-oxopurine, 2-(3,4-dichlorobenzylamino)-7-(4-iodobutyl)-6-oxopurine, 2-(3,4-dichlorobenzylamino)-7-[4-(N-morpholinyl)butyl]-6-oxopurine, 2-(3,4-dichlorobenzylamino)-7-[4-(N-piperazinyl)butyl]-6-oxopurine, 2-(3,4-dichlorobenzylamino)-7-(5-hydroxypentyl)-6-oxopurine, 2-(3,4-dichlorobenzylamino)-7-(5-methoxypentyl)-6-oxopurine, 2-(3,4-dichlorobenzylamino)-7-(5-ethoxypentyl)-6-oxopurine, 2-(3,4-dichlorobenzylamino)-7-(5-propoxypentyl)-6-oxopurine, 2-(3,4-dichlorobenzylamino)-7-(5-methylthiopentyl)-6-oxopurine, 2-(3,4-dichlorobenzylamino)-7-(5-methylsulfoxpentyl )-6-oxopurine, and 2-(3,4-dichlorobenzylamino)-7-(5-methylsulfonylpentyl)-6-oxopurine .

5. The compound of claim 1 in which n is 0, $R^3$ and $R^4$ are, independently, H, methyl, ethyl, chloro, bromo or iodo, or $R^3$ and $R^4$ together are —(CH$_2$)$_3$—.

6. The compound of claim 5 in which $R^1$ is 4-halobutyl, 4-hydroxybutyl, 4-acetoxybutyl, 4-methoxybutyl, 4-(N-morpholinyl)butyl, 4-(N-piperidinyl)butyl, 4-(N-piperazinyl)butyl, 5-methoxypentyl, 5-ethoxypentyl, 5-propoxypentyl, 5-methylthiopentyl, 5-methylsulfoxylpentyl, or 5-methylsulfonylpentyl.

7. The compound of claim 6, wherein said compound is selected from the group consisting of:

2-(3-ethyl-4-methylphenylamino)-7-(4-hydroxybutyl)-6-oxopurine, 2-(3-ethyl-4-methylphenylamino)-7-(4-acetoxybutyl)-6-oxopurine, 2-(3-ethyl-4-methylphenylamino)-7-(4-methoxybutyl)-6-oxopurine, 2-(3-ethyl-4-methylphenylamino)-7-(4-bromobutyl)-6-oxopurine, 2-(3-ethyl-4-methylphenylamino)-7-(4-iodobutyl)-6-oxopurine,
2-(3-ethyl-4-methylphenylamino)-7-[4-(N-morpholinyl)butyl]-6-oxopurine,
2-(3,4-dimethylphenylamino)-7-[4-(N-morpholinyl)butyl]-6-oxopurine,
2-(3-ethyl-4-methylphenylamino)-7-[4-(N-piperazinyl)butyl]-6-oxopurine,
2-(3-ethyl-4-methylphenylamino)-7-(5-methoxypentyl)-6-oxopurine,
2-(3-ethyl-4-methylphenylamino)-7-(5-ethoxypentyl)-6-oxopurine,
2-(3-ethyl-4-methylphenylamino)-7-(5-propoxypentyl)-6-oxopurine,
2-(3-ethyl-4-methylphenylamino)-7-(5-methylthiopentyl)-6-oxopurine,
2-(3-ethyl-4-methylphenylamino)-7-(5-methylsulfoxylpentyl)-6-oxopurine,
2-(3-ethyl-4-methylphenylamino)-7-(5-methylsulfonylpentyl)-6-oxopurine,
2-(3,4-dimethylphenylamino)-7-(4-methoxybutyl)-6-oxopurine,
2-(3-chloro-4-methylphenylamino)-7-(4-methoxybutyl)-6-oxopurine, and
2-(5-indanylamino)-7-(4-methoxybutyl)-6-oxopurine.

8. A pharmaceutical composition comprising a compound of claim 1 and a pharmaceutically acceptable carrier.

9. A method of inhibiting the growth of Gram-positive or Gram-negative bacteria, said method comprising contacting a medium or surface with an effective amount of a compound of claim 1.

10. The method of claim 9, wherein said surface is a surface of a medical device.

11. A method of treating an animal for a Gram-positive or Gram-negative bacterial infection, said method comprising administering to said animal a therapeutically effective amount of a compound of claim 1.

12. A surface coating comprising a compound of claim 1 and a coating agent, wherein said coating agent is capable of adhering said compound to a surface.

* * * * *

UNITED STATES PATENT AND TRADEMARK OFFICE
CERTIFICATE OF CORRECTION

| | | |
|---|---|---|
| PATENT NO. | : 6,926,763 B2 | Page 1 of 1 |
| APPLICATION NO. | : 10/364024 | |
| DATED | : August 9, 2005 | |
| INVENTOR(S) | : Wright et al. | |

It is certified that error appears in the above-identified patent and that said Letters Patent is hereby corrected as shown below:

Column 13, Line 55, within Scheme 1, replace "TBAl" with --TBAI-- .

Column 16, Line 45, within Scheme 4, replace "TBAl" with --TBAI-- .

Column 17, Line 40, within Scheme 5, replace "TBAl" with --TBAI-- .

Column 31, Line 44, Claim 1, replace "pharm, aceutically" with --pharmaceutically-- .

Column 31, Line 63, Claim 1, replace "$C_{1-0}$" with --$C_{1-10}$-- .

Signed and Sealed this

Third Day of July, 2007

JON W. DUDAS
*Director of the United States Patent and Trademark Office*